US010028984B2

(12) United States Patent
Yoon et al.

(10) Patent No.: US 10,028,984 B2
(45) Date of Patent: Jul. 24, 2018

(54) CLOSTRIDIUM PERFRINGENS BACTERIOPHAGE CLO-PEP-1 AND USE THEREOF FOR INHIBITING PROLIFERATION OF CLOSTRIDIUM PERFRINGENS

(71) Applicant: Intron Biotechnology, Inc., Gyeonggi-do (KR)

(72) Inventors: Seong Jun Yoon, Seoul (KR); Sang Hyeon Kang, Seoul (KR); Soo Youn Jun, Seoul (KR); Jee Soo Son, Seoul (KR); Hyoun Rok Paik, Incheon (KR); Suk Hwang Park, Gyeonggi-do (KR)

(73) Assignee: INTRON BIOTECHNOLOGY, INC., Gyeonggi-Do (KR)

( * ) Notice: Subject to any disclaimer, the term of this patent is extended or adjusted under 35 U.S.C. 154(b) by 0 days.

(21) Appl. No.: 15/538,252

(22) PCT Filed: Dec. 28, 2015

(86) PCT No.: PCT/KR2015/014326
§ 371 (c)(1),
(2) Date: Jun. 21, 2017

(87) PCT Pub. No.: WO2016/108536
PCT Pub. Date: Jul. 7, 2016

(65) Prior Publication Data

US 2017/0340685 A1 Nov. 30, 2017

(30) Foreign Application Priority Data

Dec. 29, 2014 (KR) ........................ 10-2014-0191675

(51) Int. Cl.

| | |
|---|---|
| ***A61K 35/76*** | (2015.01) |
| ***A23K 20/195*** | (2016.01) |
| ***C12N 7/02*** | (2006.01) |
| ***A61K 45/06*** | (2006.01) |

(52) U.S. Cl.
CPC ............ *A61K 35/76* (2013.01); *A23K 20/195* (2016.05); *A61K 45/06* (2013.01); *C12N 7/02* (2013.01)

(58) Field of Classification Search
None
See application file for complete search history.

(56) References Cited

U.S. PATENT DOCUMENTS 7,625,739 B2 12/2009 Pasternack et al.

FOREIGN PATENT DOCUMENTS

KR 20120076710 7/2012

OTHER PUBLICATIONS

Seal, B.S., "Characterization of bacteriophages virulent for Clostridium perfringens and identification of phage lytic enzymes as alternatives to antibiotics for potential control of the bacterium", Poultry Science,(2013), 92(2): 526-533.
International Search Report and Written Opinion were dated Apr. 25, 2016 by the International Searching Authority for International Application No. PCT/KR2015/014326, which was filed on Dec. 28, 2015 and published as WO/2016/108536 on Jul. 7, 2016 (Applicant-Intron Biotechnology, Inc.) (Original-9 pages// Translation—2 pages).

*Primary Examiner* — Michelle S Horning
(74) *Attorney, Agent, or Firm* — Ballard Spahr LLP

(57) ABSTRACT

The present invention relates to a Myoviridae bacteriophage Clo-PEP-1 that is isolated from the nature and can kill *Clostridium perfringens* cells specifically, which has the genome represented by nucleotide sequence of SEQ. ID. NO: 1 (Accession NO: KCTC 12664BP), and a method for preventing and treating the infections of *Clostridium perfringens* cells using the composition comprising said bacteriophage as an active ingredient.

2 Claims, 1 Drawing Sheet

CLOSTRIDIUM PERFRINGENS BACTERIOPHAGE CLO-PEP-1 AND USE THEREOF FOR INHIBITING PROLIFERATION OF CLOSTRIDIUM PERFRINGENS

CROSS-REFERENCE TO RELATED APPLICATIONS

The present application is a U.S. National Phase Application of International Application No. PCT/KR2015/014326, filed Dec. 28, 2015, which claims priority to Korean Application No. 10-2014-0191675, filed Dec. 29, 2014, each of which are hereby incorporated by reference in their entirety.

REFERENCE TO SEQUENCE LISTING

The Sequence Listing submitted Jul. 14, 2017, as a text file named "08162_0029U1_Revised_Sequence_Listing.txt" created on Jul. 13, 2017, and having a size of 66,111 bytes is hereby incorporated by reference pursuant to 37 C.F.R. § 1.52(e)(5).

BACKGROUND OF THE INVENTION

1. Field of the Invention

The present invention relates to a bacteriophage isolated from the nature that infects and kills *Clostridium perfringens* cells, and a method for preventing and treating the infections of *Clostridium perfringens* cells using a composition comprising the bacteriophage as an active ingredient. More particularly, the present invention relates to a Myoviridae bacteriophage Clo-PEP-1 that is isolated from the nature and can kill *Clostridium perfringens* cells specifically, which has the genome represented by nucleotide sequence of SEQ. ID. NO: 1 (Accession NO: KCTC 12664BP), and a method for preventing the infections of *Clostridium perfringens* cells and thereafter treating them using the composition comprising said bacteriophage as an active ingredient.

2. Description of the Related Art

*Clostridium perfringens* is an obligatory anaerobe (rarely survived in the presence of oxygen) and pathogenic bacterium that causes severe diseases including necrotic enteritis and food poisoning in human and animals such as cow, pig and goat etc. Enterotoxins produced by *Clostridium perfringens* are usually hemolytic toxins and nectrotic toxins, which comprises four kinds of major toxins, $\alpha$, $\beta$, $\varepsilon$ and $\iota$. According to their presence, *Clostridium perfringens* is classified to six toxigenic types, A to F. *Clostridium perfringens* type A is a major causative pathogen of food poisoning, and *Clostridium perfringens* type C is a major causative pathogen of necrotic enteritis.

Recently, the infections of *Clostridium perfringens* are increasingly provoked in poultry industry. Thus chicken yards are being suffered from these cases, because they become prevalent in a large population of chickens as well as latent without manifestation of symptoms for a long time period. Especially in broiler chickens, the infections of *Clostridium perfringens* tends to often occur world-widely, so that it is recognized deeply as a main pathogen nowadays. Moreover, it is reported in pig farming industry that the infectious cases of *Clostridium perfringens* are increasing. Considering a significant damage in livestock industry by such *Clostridium perfringens*, it is urgently requested to develop a method for preventing or treating the infections of *Clostridium perfringens*. A variety of antibiotics have been used to prevent or treat such infections of *Clostridium perfringens* cells. However, according to the recent rise of antibiotic-resistant bacteria, an efficient alternative is urgently requested.

Recently, the use of bacteriophages has drawn our attention as a new way of treating bacterial infections. Particularly, the reason of our high interest in bacteriophages is because bacteriophage-based treatment is a nature-friendly method.

Bacteriophages are an extremely small microorganism that infects bacteria, which are called phage in short. Once bacteriophage infects bacteria, the bacteriophage is proliferated in the inside of the bacterial cell. After full proliferation, the progenies destroy the bacterial cell wall to escape from the host, suggesting that the bacteriophage has bacteria killing ability. The bacteriophage infection is characterized by high specificity, so that a certain bacteriophage infects only a specific bacterium. That is, the bacterium that can be infected by certain bacteriophage is limited, suggesting that bacteriophage can kill only a specific bacterium and cannot harm other bacteria.

Bacteriophage was first found out by an English bacteriologist Twort in 1915 when he noticed that Micrococcus colonies melted and became transparent by something unknown. In 1917, a French bacteriologist d'Herelle found out that *Shigella disentriae* in the filtrate of dysentery patient feces melted by something, and further studied about this phenomenon. As a result, he identified bacteriophage independently, and named it as bacteriophage which means a bacteria killer. Since then, bacteriophages specifically acting against such pathogenic bacteria as *Shigella, Salmonella Typhi*, and *Vibrio cholerae* have been continuously identified.

Owing to the unique capability of bacteriophage to kill bacteria, bacteriophages have been studied and anticipated as a better method to treat bacterial infections. However, after penicillin was found by Fleming, studies on bacteriophages had been only continued in some of Eastern European countries and the former Soviet Union because of the universalization of antibiotics. After the year of 2000, the merit of the conventional antibiotics faded because of the increase of antibiotic-resistant bacteria. So, bacteriophages are once again spotlighted as a new anti-bacterial agent that can replace the conventional antibiotics.

Furthermore, the recent regulation of using antibiotics is fortified by the government world-widely. The interest on bacteriophages is increasing more and also industrial applications are increasily achieved.

Therefore, the present inventors tried to develop a composition applicable for the prevention or treatment of *Clostridium perfringens* infections by using a bacteriophage that is isolated from the nature and can kill *Clostridium perfringens* selectively and further to establish a method for preventing or treating the infections of *Clostridium perfringens* using the composition. As a result, the present inventors isolated bacteriophages suitable for this purpose and secured the nucleotide sequence of the genome that can distinguish the bacteriophage of the present invention from other bacteriophages. Then, we have developed a composition comprising the isolated bacteriophage as an active ingredient, and confirmed that this composition could be efficiently used for the prevention and treatment of *Clostridium perfringens* infections, leading to the completion of the present invention.

SUMMARY OF THE INVENTION

It is an object of the present invention to provide a Myoviridae bacteriophage Clo-PEP-1 that is isolated from the nature and can kill *Clostridium perfringens* cells specifically, which has the genome represented by the nucleotide sequence of SEQ. ID. NO: 1 (Accession NO: KCTC 12664BP).

It is another object of the present invention to provide a composition applicable for the prevention of *Clostridium perfringens* infections, which comprises the bacteriophage Clo-PEP-1 that can infect and kill *Clostridium perfringens* cells as an active ingredient and a method for preventing the infections of *Clostridium perfringens* using said composition.

It is another object of the present invention to provide a composition applicable for the treatment of *Clostridium perfringens* infections, which comprises the bacteriophage Clo-PEP-1 that can infect and kill *Clostridium perfringens* cells as an active ingredient and a method for treating the infections of *Clostridium perfringens* using said composition.

It is another object of the present invention to provide a disinfectant for preventing and treating the infections of *Clostridium perfringens* using said composition.

It is another object of the present invention to provide a drinking water additive for preventing and treating the infections of *Clostridium perfringens* using said composition.

It is also an object of the present invention to provide a feed additive effective on farming by preventing and treating the infections of *Clostridium perfringens* using said composition.

To achieve the above objects, the present invention provides a Myoviridae bacteriophage Clo-PEP-1 that is isolated from the nature and can kill *Clostridium perfringens* cells specifically, which has the genome represented by the nucleotide sequence of SEQ. ID. NO: 1 (Accession NO: KCTC 12664BP), and a method for preventing and treating the infections of *Clostridium perfringens* using a composition comprising the bacteriophage as an active ingredient.

The bacteriophage Clo-PEP-1 has isolated by the present inventors and then deposited at Korean Collection for Type Cultures, Korea Research Institute of Bioscience and Biotechnology in Aug. 21, 2014 (Accession NO: KCTC 12664BP). The present invention also provides a disinfectant, a drinking water additive, and a feed additive applicable for the prevention or treatment of *Clostridium perfringens* infections, which comprises the bacteriophage Clo-PEP-1 as an active ingredient.

Since the bacteriophage Clo-PEP-1 included in the composition of the present invention kills *Clostridium perfringens* cells efficiently, it is regarded as effective to prevent or treat various diseases caused by *Clostridium perfringens*. Therefore, the composition of the present invention can be utilized for the prevention and treatment of diseases (infections) caused by *Clostridium perfringens*.

In this description, the term "treatment" or "treat" indicates (i) to suppress diseases caused by *Clostridium perfringens* cells; and (ii) to relieve diseases caused by *Clostridium perfringens* cells.

In this description, the term "isolation" or "isolated" indicates all the actions to separate the bacteriophage by using diverse experimental techniques and to secure the characteristics that can distinguish this bacteriophage from others, and further includes the action of proliferating the bacteriophage via bioengineering techniques so as to make it useful.

The pharmaceutically acceptable carrier included in the composition of the present invention is the one that is generally used for the preparation of a pharmaceutical formulation, which is exemplified by lactose, dextrose, sucrose, sorbitol, mannitol, starch, acacia rubber, calcium phosphate, alginate, gelatin, calcium silcate, microcrystalline cellulose, polyvinyl pyrrolidone, cellulose, water, syrup, methylcellulose, methylhydroxybenzoate, propylhydroxybenzoate, talc, magnesium stearate, and mineral oil, but not always limited thereto. The composition of the present invention can additionally include lubricants, wetting agents, sweeteners, flavors, emulsifiers, suspending agents, and preservatives, in addition to the above ingredients.

In the composition of the present invention, the bacteriophage Clo-PEP-1 is included as an active ingredient. At this time, the bacteriophage Clo-PEP-1 is included at the concentration of $1\times10^{1}$ pfu/ml~$1\times10^{30}$ pfu/ml or $1\times10^{1}$ pfu/g~$1\times10^{30}$ pfu/g, and preferably at the concentration of $1\times10^{4}$ pfu/ml~$1\times10^{15}$ pfu/ml or $1\times10^{4}$ pfu/g~$1\times10^{15}$ pfu/g.

The composition of the present invention can be formulated by the method that can be performed by those in the art by using a pharmaceutically acceptable carrier and/or excipient in the form of unit dose or in a multi-dose container. The formulation can be in the form of solution, suspension or emulsion in oil or water-soluble medium, extract, powder, granule, tablet or capsule. At this time, a dispersing agent or a stabilizer can be additionally included.

The composition of the present invention can be prepared as a disinfectant, a drinking water additive, or a feed additive according to the purpose of use, but not always limited thereto.

Advantageous Effect

The method for preventing and treating the infections of *Clostridium perfringens* using this composition comprising the bacteriophage Clo-PEP-1 as an active ingredient, have the advantage of high specificity to *Clostridium perfringens*, compared with the conventional methods based on the chemical materials including the conventional antibiotics. That means, the composition of the present invention can be used for preventing or treating the infections of *Clostridium perfringens* specifically without affecting other useful residential bacteria, and accordingly has fewer side effects. In general, when chemical materials such as antibiotics are used, the general residential bacteria are also damaged to weaken immunity in animals with carrying various side effects. In the meantime, the composition of the present invention uses the bacteriophage isolated from the nature as an active ingredient, so that it is very nature-friendly.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
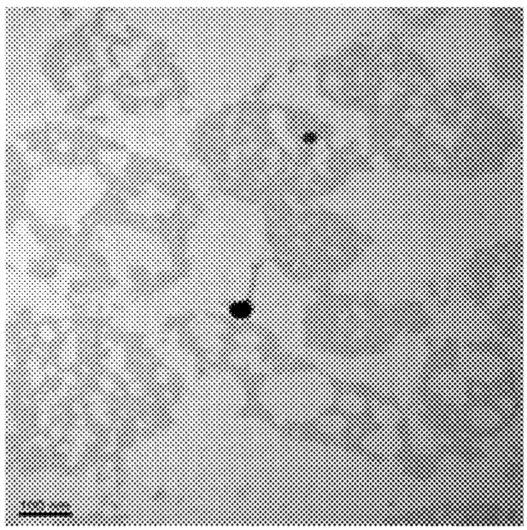
FIG. 1 is an electron micrograph showing the morphology of the bacteriophage Clo-PEP-1.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Isolation of Bacteriophage Capable of Killing *Clostridium perfringens* Cells Samples were collected from the nature to screen the bacteriophage having the capability to kill *Clostridium perfringens* cells. The *Clostridium perfringens* cells used for the bacteriophage isolation herein were the one that had been isolated by the present inventors and identified as *Clostridium perfringens* previously.

The isolation procedure of the bacteriophage is described in detail hereinafter. The collected sample was added to the TSB (Tryptic Soy Broth) medium (pancreatic digest of casein, 17 g/L; papaic digest of soybean, 3 g/L; dextrose, 2.5 g/L; sodium chloride, 5 g/L; dipotassium phosphate, 2.5 g/L) inoculated with *Clostridium perfringens* cells at the ratio of 1/1000, followed by anaerobic culturing at 37° C. for 12 hours. Upon completion of the culture, centrifugation was performed at 8,000 rpm for 20 minutes and supernatant was recovered. The recovered supernatant was inoculated with *Clostridium perfringens* culture at the ratio of 1/1000, followed by anaerobic culturing at 37° C. for 12 hours. When the sample contained the effective bacteriophage, the above procedure was repeated total 5 times in order to increase the titer of the bacteriophage. After repeating the procedure 5 times, the culture solution proceeded to centrifugation at 8,000 rpm for 20 minutes and the resulting supernatant was recovered. The recovered supernatant was filtrated by using a 0.45 μm filter. The obtained filtrate was used in spot assay for examining whether or not the bacteriophage capable of killing *Clostridium perfringens* cells was included therein.

Spot assay was performed as follows; TSB medium was inoculated with *Clostridium perfringens* cells at the ratio of 1/1000, followed by anaerobic culturing at 37° C. for overnight. 3 ml ($OD_{600}$=2.0) of the culture broth of *Clostridium perfringens* prepared above was spread on the TSA (Tryptic Soy Agar; pancreatic digest of casein, 17 g/L; papaic digest of soybean, 3 g/L; sodium chloride, 5 g/L; agar, 15 g/L) plate. The plate stood in an anaerobic chamber for about 30 minutes to dry. After drying, 10 μl of the resulting filtrate was spotted directly onto the surface of the *Clostridium perfringens* lawns and dried for about 30 minutes. Following drying, the plate was incubated at 37° C. under an anaerobic condition for a day and then, examined for the formation of clear zones on the surface of the bacterial lawns. If a clear zone was generated where the filtrate was dropped, it could be judged that the bacteriophage capable of killing *Clostridium perfringens* cells was included in the filtrate. Through the above procedure, the filtrate containing the bacteriophage capable of killing *Clostridium perfringens* cells could be obtained.

After that, the bacteriophage was isolated from the filtrate confirmed above to have the bacteriophage capable of killing *Clostridium perfringens* cells. The conventional plaque assay was used for the isolation of pure bacteriophages. In detail, a plaque formed in the course of the plaque assay was picked up by using a sterilized tip, which was then added to the culture solution of *Clostridium perfringens*, followed by culturing under an anaerobic condition at 37° C. for 12 hours. Upon completion of the culture, centrifugation was performed at 8,000 rpm for 20 minutes to obtain supernatant. The recovered supernatant was inoculated with *Clostridium perfringens* culture at the ratio of 1/50, followed by culturing under an anaerobic condition at 37° C. for 12 hours. To increase the titer of the bacteriophage, the above procedure was repeated at least 5 times. Then, centrifugation was performed at 8,000 rpm for 20 minutes to obtain supernatant. Plaque assay was performed with the obtained supernatant. In general, the pure bacteriophage isolation is not completed by one-time procedure, so the above procedure was repeated by using the plague formed above. After at least 5 times of repeated procedure, the solution containing the pure bacteriophage was obtained. The procedure for the isolation of the pure bacteriophage was generally repeated until the generated plaques became similar in sizes and morphologies. And the final pure bacteriophage isolation was confirmed by the observation under electron microscope. Until the pure bacteriophage isolation was confirmed under electron microscope, the above procedure was repeated. The observation under electron microscope was performed by the conventional method. Briefly, the solution containing the pure bacteriophage was loaded on copper grid, followed by negative staining with 2% uranyl acetate. After drying thereof, the morphology was observed under transmission electron microscope. The electron micrograph of the bacteriophage isolated in the present invention is presented in FIG. 1. From the morphological observation, the bacteriophage isolated above was identified as belonging to the family Myoviridae.

The solution containing the pure bacteriophage confirmed above proceeded to purification. The culture broth of *Clostridium perfringens* cells was added to the solution containing the pure bacteriophage at the volume of 1/50 of the total volume of the bacteriophage solution, followed by culturing again for 12 hours. Upon completion of the culture, centrifugation was performed at 8,000 rpm for 20 minutes to obtain supernatant. This procedure was repeated 5 times to obtain a solution containing enough numbers of the bacteriophage. The supernatant obtained from the final centrifugation was filtered by a 0.45 μm filter, followed by the conventional polyethylene glycol (PEG) precipitation. Particularly, PEG and NaCl were added to 100 ml of the filtrate until reaching 10% PEG 8000/0.5 M NaCl, which stood at 4° C. for 2~3 hours. Then, centrifugation was performed at 8,000 rpm for 30 minutes to obtain the bacteriophage precipitate. The resulting bacteriophage precipitate was resuspended in 5 ml of buffer (10 mM Tris-HCl, 10 mM $MgSO_4$, 0.1% Gelatin, pH 8.0). This solution was called as the bacteriophage suspension or bacteriophage solution.

As a result, the pure bacteriophage purified above was collected, which was named as the bacteriophage Clo-PEP-1 and then deposited at Korean Collection for Type Cultures, Korea Research Institute of Bioscience and Biotechnology in Aug. 21, 2014 (Accession NO: KCTC 12664BP).

Example 2: Separation and Sequence Analysis of the Bacteriophage Clo-PEP-1 Genome The genome of the bacteriophage Clo-PEP-1 was separated as follows. The genome was separated from the bacteriophage suspension obtained in Example 1. First, in order to eliminate DNA and RNA of *Clostridium perfringens* cells included in the suspension, DNase I and RNase A were added 200 U each to 10 ml of the bacteriophage suspension, which was incubated at 37° C. for 30 minutes. 30 minutes later, to remove the DNase I and RNase A activity, 500 μl of 0.5 M ethylenediaminetetraacetic acid (EDTA) was added thereto, which was incubated for 10 minutes. The suspension was further incubated at 65° C. for 10 minutes and then added with 100 μl of proteinase K (20 mg/10) to break the outer wall of the bacteriophage, followed by incubation at 37° C. for 20 minutes. After that, 500 μl of 10% sodium dodecyl sulfate (SDS) solution was added thereto, followed by incubation at 65° C. for 1 hour. 10 ml of the mixture of phenol:chloroform:isoamylalcohol in a ratio of 25:24:1 was added thereto, followed by mixing well. The mixture was centrifuged at 13,000 rpm for 15 minutes to separate each layer. The upper layer was obtained, to which isopropyl alcohol was added at the volume of 1.5 times the volume of the upper layer, followed by centrifugation at 13,000 rpm for 10 minutes to precipitate the genome of the bacteriophage. After collecting the precipitate, 70% ethanol was added to the precipitate, followed by centrifugation at 13,000 rpm for 10 minutes to wash the precipitate. The washed precipitate was recovered, vacuum-dried and then dissolved in 100 μl of water. This procedure was repeated to obtain a sufficient amount of the bacteriophage Clo-PEP-1 genome.

The nucleotide sequence of the genome of the bacteriophage Clo-PEP-1 obtained above was analyzed by Next Generation Sequencing (NGS) using illumina Mi-Seq device at National Instrumentation Center for Environmental Management, Seoul National University. As a result, it is suggested that the final genome of bacteriophage Clo-PEP-1 has 50,401 bp of size and the nucleotide sequence of the whole genome has SEQ. ID. NO: 1.

Similarity of the genomic sequence of the bacteriophage Clo-PEP-1 obtained above with the previously reported bacteriophage genome sequences of was investigated by using BLAST. From the BLAST result, it was difficult to find bacteriophage sequences having more than 50% of sequence homology with this bacteriophage sequence. Based upon this result, the bacteriophage Clo-PEP-1 is concluded that the bacteriophage Clo-PEP-1 should be a novel bacteriophage not reported previously.

Example 3: Investigation of Killing Ability of the Bacteriophage Clo-PEP-1 Against *Clostridium perfringens*

Figure 2:
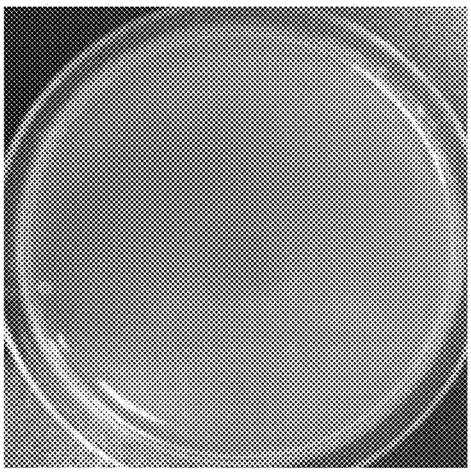
FIG. 2 is a photograph illustrating the capability of the bacteriophage Clo-PEP-1 to kill *Clostridium perfringens* cells. The clear zone on the dish is the formation of plaque by lysis of bacteria cells.

The killing ability of the isolated bacteriophage Clo-PEP-1 against *Clostridium perfringens* was investigated. To do so, the formation of clear zone was observed by the spot assay by the same manner as described in Example 1. The *Clostridium perfringens* cells used for this investigation were total 15 strains which had been isolated and identified as *Clostridium perfringens* previously by the present inventors. The bacteriophage Clo-PEP-1 demonstrated the killing ability against 12 strains of *Clostridium perfringens* cells used in this experiment. The representative result of the killing ability test is shown in FIG. 2. In the meantime, the activity of the bacteriophage Clo-PEP-1 to kill *Pasteurella multocida, Haemophilus parasuis, Bordetella bronchiseptica, Enterococcus faecalis, Enterococcus faecium, Streptococcus suis, Streptococcus uberis* and *Pseudomonas aeruginosa* was also investigated. As a result, it is decided that the bacteriophage Clo-PEP-1 did not have the killing activity against these microorganisms.

Therefore, it was confirmed that the bacteriophage Clo-PEP-1 has the specific ability to kill *Clostridium perfringens* cells and a broad antibacterial spectrum against *Clostridium perfringens*, suggesting that the bacteriophage Clo-PEP-1 of the present invention could be used as an active ingredient of the composition for the prevention and treatment of *Clostridium perfringens* infections.

Example 4: Preventive Effect of Bacteriophage Clo-PEP-1 on the Infections of *Clostridium perfringens*

100 μl of the bacteriophage Clo-PEP-1 solution at $1\times10^9$ pfu/ml was added to a tube containing 9 ml of TSB. To another tube containing 9 ml of TSB, only the same volume of TSB was added. Then, the *Clostridium perfringens* culture was added to each tube to prepare bacterial suspension in 0.5 of $OD_{600}$. After that, the tubes were transferred to an anaerobic incubator at 37° C., followed by culturing, during which the growth of *Clostridium perfringens* cells was observed. As presented in Table 1, the growth of *Clostridium perfringens* cells was inhibited in the tube added with the bacteriophage Clo-PEP-1 solution, while the growth of *Clostridium perfringens* cells was not inhibited in the tube without the bacteriophage Clo-PEP-1 solution.

TABLE 1

Inhibition of growth of *Clostridium perfringens*

| Item | $OD_{600}$ Culturing 0 min. | Culturing 60 min. | Culturing 90 min. |
|---|---|---|---|
| (−) bacteriophage solution | 0.5 | 0.9 | 1.2 |
| (+) bacteriophage solution | 0.5 | 0.3 | 0.2 |

The above results indicate that the bacteriophage Clo-PEP-1 not only inhibits the growth of *Clostridium perfringens* cells but also can kill them. Therefore, the bacteriophage Clo-PEP-1 can be used as an active ingredient of the composition for preventing the infections of *Clostridium perfringens*.

Example 5: Therapeutic Effect of Bacteriophage Clo-PEP-1 on the Infections of *Clostridium perfringens*

Therapeutic effect of the bacteriophage Clo-PEP-1 on animals affected by *Clostridium perfringens* cells was investigated. 40 chicks at 2 days of age were orally administered with $1\times10^7$ cfu of *Clostridium perfringens* cells to infect animals. They were divided to 2 groups randomly. One experimental group was fed with mixing $1\times10^8$ pfu of bacteriophage Clo-PEP-1 per 1 g of feeds. The other control group was fed via the same way without bacteriophage Clo-PEP-1. After 2 days of challenge, the number of *Clostridium perfringens* cells within the contents of animal feces and caecum was measured. In this measurement, in order to escape the intervention of other contaminating bacteria, selective medium (TSC agar plate: OXOID) for *Clostridium perfringens* cells was used. As a result, it is demonstrated that the experimental group fed with bacteriophage Clo-PEP-1, should decrease *Clostridium perfringens* cells in the content of feces more than 500 times and in the content of caecum more than 300 times, compared to the control group without the bacteriophage Clo-PEP-1.

From the above results, it was confirmed that the bacteriophage Clo-PEP-1 of the present invention could be very effective to treat infectious diseases caused by *Clostridium perfringens.*

Example 6: Preparation of Feed Additives and Feeds

Feed additive containing bacteriophage Clo-PEP-1 at a concentration of $1\times10^8$ pfu/g was prepared using the bacteriophage Clo-PEP-1 solution. The preparation method thereof was as follows: Maltodextrin (40%, w/v) was added to the bacteriophage solution and then, trehalose was added to 10% of final concentration. After mixing well, the mixture was freeze-dried. Lastly, the dried mixture was grinded into fine powders. The drying process above can be replaced with vacuum-drying, drying at warm temperature, or drying at room temperature. To prepare the control feed additive for comparison, feed additive that did not contain the bacteriophage but contained buffer (10 mM Tris-HCl, 10 mM $MgSO_4$, 0.1% Gelatin, pH 8.0) only was prepared.

The above two kinds of feed additives were mixed with the 1000 times volume of feed for chicken farming respectively, resulting in two kinds of final feeds.

Example 7: Preparation of Drinking Water Additives and Disinfectants

Drinking water additive and disinfectant are different in intended use but same in the composition, so they have been prepared by the same manner. Drinking water additive (or disinfectant) containing bacteriophage Clo-PEP-1 at a concentration of $1\times10^8$ pfu/ml was prepared using the bacteriophage Clo-PEP-1 solution. Particularly, to prepare drinking water additive (or disinfectant), the bacteriophage Clo-PEP-1 solution was added to buffer solution to reach $1\times10^8$ pfu/ml, which was mixed well. For the comparison, the above buffer solution itself was used as the drinking water additive (or disinfectant) that did not contain the bacteriophage.

The prepared two kinds of drinking water additives (or disinfectants) were diluted in water at the ratio of 1:1000, and then used as drinking water or disinfectant.

Example 8: Effect on Chicken Farming

The effect of the feeds, drinking water, and disinfectant prepared in Example 6 and Example 7 on chicken farming was investigated. Particularly, the investigation was focused on mortality. Total 120 chicks at 2 days of age were grouped into three groups, and each group was composed of 40 chicks (group A: feed test group, group B: drinking water test group; and group C: disinfectant test group). The experiment was continued for 4 weeks. Each group was divided by two sub-groups comprising 20 chicks each. The sub-groups were divided according to the treatment of the bacteriophage Clo-PEP-1 or not (sub-group-①: treated with the bacteriophage Clo-PEP-1; and sub-group-②: not-treated with the bacteriophage Clo-PEP-1). The chicks used in this experiment were separated to each sub-group and raised in a separated room placed at a sufficient distance from each other. Each sub-group was divided and named as shown in Table 2.

TABLE 2

Sub-groups of chicken farming experiment

| | Sub-group | |
|---|---|---|
| Item | Treated with the bacteriophage Clo-PEP-1 | Not-treated with the bacteriophage Clo-PEP-1 |
| Fed with feeds | A-① | A-② |
| Provided with drinking water | B-① | B-② |
| Treated with disinfectant | C-① | C-② |

Feeds were provided according to the conventional feed supply method as presented in Table 2 with the feeds prepared in Example 6. Drinking water was provided according to the conventional water supply method as presented in Table 2 with the drinking water prepared in Example 7. Disinfectant was treated to chickens three times a week with taking turns with the conventional disinfectant. That is, on the day when the disinfectant of the present invention was sprayed, the conventional disinfectant was not treated. The results are shown in Table 3.

TABLE 3

Mortality of chicken farming experiment

| Group | Mortality (%) |
|---|---|
| A-① | 0 |
| A-② | 40 |
| B-① | 5 |
| B-② | 35 |
| C-① | 0 |
| C-② | 35 |

From the above results, it was confirmed that the feeds, drinking water, and the disinfectant prepared according to the present invention were effective in reducing the animal mortality. Therefore, it is concluded that the composition of the present invention could be efficiently applied for the improvement of productivity of animal farming.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for preventing or treating a *Clostridium perfringens* infection, which comprises a step of administering to a subject a composition comprising Myoviridae bacteriophage Clo-PEP-1, wherein said bacteriophage comprises the nucleotide sequence of SEQ ID NO: 1 as an active ingredient.

2. The method for preventing or treating a *Clostridium perfringens* infection according to claim 1, wherein the composition is administered to a subject in the form of a feed additive, a drinking water additive, or a disinfectant.

* * * * *

SEQUENCE LISTING

```
<160> NUMBER OF SEQ ID NOS: 1

<210> SEQ ID NO 1
<211> LENGTH: 50401
<212> TYPE: DNA
```

-continued

<213> ORGANISM: Bacteriophage Clo-PEP-1

<400> SEQUENCE: 1

```
attagaatac ccccttaata tctttgttgt aaacatgaag agagaaaatt gtatgagaga     60
aacttcctgg ttcatagcca gtttgttcag ctacccaatg taatagtttc atagcaagat    120
aaacatcatt agcaaagtga gtagcaaagt cagagcttct cataacataa tgaatattta    180
atttaccttc ccttacttgg aagttatatc ctaatgaaca tggtactcta gttactcctc    240
ctatattgaa tggatcaata gctggattcc acagagataa ccataattgt cttgagcctg    300
gatcttcttt aattctattg atgatatctt caatttgtct gtattgccaa attctttcat    360
tgtaagaata tccaaatttc ccatctctta gatactcatt ccatacctca ggtcttaatt    420
gataagcttt acctggattg atgaaagcct ccctagtatg atgtggaggt ataccaaata    480
attcttctct ttcttcaaga gagtattgat tgatgacacc ttgtggatcg tagatccttt    540
ctctaaattc agcatctgcc caaggttgag atacacctgg aacttcttca ggtttacttt    600
ctagaattgt ataactatag ttttgtaact cctttgtgaa ataatctgga ttaccttcta    660
taactttatc ttgcatagtt ttgggtctta cctcaatccc catttcacat aaatctcttt    720
ttacttcttc aaatgcttct tgagcattaa tataaattct catagtttaa ttcctccatt    780
tattgaattt tgttaagtta attatactac ttattaaagt acttgtcaat agataattta    840
ttgatatcta tctttggaaa tttctccaga ccaaaatgta ataactgcat cttctggaga    900
gctttgtaag agtgtatctg gtcctctgat ttaaagaacc tattatagtt actattcaag    960
gatttatgcc aaggatgttt actattagca atactctttc ttggtacctt aaaataattg   1020
aagtatccat ttataaacat tcctgacaaa taagcttgag acatatgaaa agtaatatta   1080
tctatctcac atacttcttg aggtagttct tcaatgaacc tgtttattaa tactagatca   1140
gctgcgaatt tcttttgcaa ttcacatact ctatacataa tttttaagtg tttccaaggt   1200
ccttttcttt ttggtctagt tactactgca gctatcaagc aagaaccatt agtagctttt   1260
ttcctgttga aataataagt atagctcata ccacttatct tggtaagctt ttctctaaat   1320
tcaattaatt gtggataatc aatgtatgat cttaataggt gtccccactt accttcttta   1380
tatccaaagt cccctagatt taaagtacat ttatgggact tacaggagag aactaagtcc   1440
tcctgaaagc cctgtatgtt ctgagtatac atcatagttt cttctggatt ggtaatcatt   1500
tccctattaa gatttaagaa taagtcatca aaatcattat agtctcttat tagcatatta   1560
ccttctccta agtatttatt ttagtaatta gatctttggc ggaatttatt tacctgtgat   1620
ttcttaaggt atatatttac tatgtcatct acctctaagc cagatacagc taataattta   1680
atgtaacata tccatacatt gaatagtctt tgattaaagg catttacatc tgttagcatt   1740
gaagtttgtt tccaaggttt attcttaagg cagttacagc acatacctat ttctctcact   1800
aagtcagtta cagccttttc cacacaaggt ttatcttcat catttactat agcttggtaa   1860
tataagtttg ctaggtgatc ttttcctact ttgttcactg gatctatagt attataatcc   1920
ttaccagcta ggattgtaaa ttcagttaag aagtgtaatc catcaatcaa ttcttcttgg   1980
taatggtctt catggttata agcatctaat gcttctccta cttcttcagt cattctccaa   2040
gcaaaatcct taagtctagc ttgacctctt ttatcattta agttaactgg acagtcttca   2100
gtttggcata atcctgatct agcttctata tgatgatatt tctccatcaa ttccttttgt   2160
ctattaaaga tagcttgtaa tctatctcct tctacttttt cttctactgc atggtttata   2220
ttcataacaa tctctcctct tatcttgata tatttataaa ttggtttata gcttctttag   2280
```

-continued

```
cacttgagtc atctattaat tgggatagct tctccacatt ggaagtagta taatcatata   2340
ccagtacatt ccatccatca cagaataatt tccatatcag ttcatcatat ctagccagta   2400
gatgttcagc tctttcaatt actcctggca tctgttctct atcaccaaaa ttgaagatca   2460
cttccctagg tggtctagca tatacaatag ttggcttaca tagatgtttt aagatcttta   2520
gctccttact gtcaaggttg aaattactac tatctctgat gataggtcca tacaccattt   2580
cttcaaagca agtaaatcta tcatgtatag cttccctttc acctttctc acaatttgag    2640
ttaataccca ttctctttgt tcttcataag aaccaggtcc cattgattgg atatattctc   2700
ctcctctgtg tttagttagg ttcttagctg ttgtggtctt acctgagtta tccattccta   2760
aaatgataat cattaaagct ctcctccatt ctttagatct tctactatta agtttagtat   2820
atattgtact cctttatcat tatattcaaa taaaggattt ataagggact tacttggagt   2880
tacataataa ccaagttctt tagcaaggat tgggtctatt atttcaagtg tatgctcatt   2940
gtaccttctg gcaaatccct ttcttactaa atacctattt agttttatca cactaactcc   3000
taatgctcct gctatcttag tagcagtggt taaacttccc ttccataatt ggggtttgtc   3060
atcattaagg tctttcaaga tgtaatactt tttcttgacc attaaattct cctccttcta   3120
catttttata ttaccataat taatttatta tgtcaaaggt tattttagaa tttttaggta   3180
tatctataac agccagaaga ttttctggtc tattactatc ataaacaagt atagtataat   3240
tctgagctcc taagttattg accataacct cattagctaa cttagataaa ttgttagggg   3300
taaggtcttt aggactatta aggtttagtt tgataataag atcctcccca tctagtccag   3360
atggagaagt ctcaataaca ttatagtcta aagcattatg aagcttttct actaactttt   3420
cttgactttt tctttggtga tgaccttcta ttagttttgc cccctgagtt agcattatcc   3480
ccattgacaa tgatatccct agaattagta ctacttcctt caagtttctt cttcgcatta   3540
gccttagcct ccctatactt tatattcata catttacat aaaagtcttg gtcacttata    3600
ccacagatag ggcaattctt gtaacctcct tggcttctct taaattcttg aatagtttga   3660
caatatggac accacatctt ctttttaggt atttcttcgc cttcagggat cttatgagct   3720
tcatggacat ccacccaata aaattcagcc cagggacatt cttccataac tttgtctata   3780
aataatttag ctgatttata ggtatagaaa tatttcaatc ctgaatgata agtgatttta   3840
ttcttcttac ctctagcaat aattactact acaaaggcct ttatatgatt atgacctgct   3900
ggcctcttac actttattat catgcctttt tcctccccat atttagtttc ttacttatat   3960
tataaccttt atccggagaa tatacaatag tatcttttaa agtatctaga actagattaa   4020
ccttctgtga atttaatcct gatattgaca ctatctcctc cttagtatga gctcctgatt   4080
ttacagcctc tataactttg gctttgtcct caggtttcac aattacttct tttccaggta   4140
ttgctacttc tacatgataa tatggatccc caaattctcc cattgataaa tttaattcaa   4200
tttgagggaa ttgtcctgca agacggaact ctctatccat aatgatttta cttggtaaat   4260
ggctttgttt atcaaggtta tctatatcta cctcgatctc ctcatcgtca ccttctaagt   4320
catcaggtct ttttaaatat agtgctgatt ctacccaacc atgtaatatg aatgaaccag   4380
ccatcttttg accaccccta gtttgagtag catttccacc tttattatag tggtgtatta   4440
acataactcc tgtatgcttc tcattcttaa gtttaagaca ccattgtagt acaggattaa   4500
gatcagctgc attattaaga tctccactaa acataagata taatgggtcg aatattacta   4560
gtacgggttt tatctcatca attaaatctt ctatctgttt tctatgggat tcttcatcta   4620
```

-continued

```
acataaatcc ctgttgatta ataaaagtga taggaagatc tggagcaaac ctaactttaa   4680
gtcttctctt accttttata tccacattac caactactcc tctgtggcta attatctttt   4740
cagttctatc tctcataatc cagtcagcat tctcattttg aactacaatt actgggcctg   4800
gttctagaac aggatattga cctaggaatg gtcttccact agcaactgat atagctaagt   4860
cctgtgtaaa tgtggattta aataccttg gttgtccagc cacaattcca tgagatcttc   4920
taccccagaa accttgtact aaccaaccag ggaaggctcc attattaccc ataacatcct   4980
gataactatc tattctcagt ttagtacttt cagctttttc aatatcagcc tctatttctc   5040
ctcctataat tttatccaat tcttttctta accttgtttc ttcatctttt cttcccttat   5100
atttattaaa agctgagccc ttaactaata atataatctc attaggctct agtcctattt   5160
catgtaattt attctcaata taccatatag tagaacttct atctaaagaa gtaatatcat   5220
ctaaagccag taagtctcta accttctttg gtatattata tttagcatat atctttcttt   5280
cagattgtga ggcctcagat cctcctatat tgaccttaac actatcatta gatttactta   5340
cagccttaac agccttagcg atcaccttag gcttatatat ctccttagtg tgtataggtc   5400
tttttacttt tggtttattc ttgtatttgt agttaatagt tcctggtatt ctatatacat   5460
gagtaacatc aaagcaggag tcacagccta tatgtttagc taatgctgga tttatttcgt   5520
catactgatt agcctctata tacctatcca tttcccatag cccctgatat tttccaggag   5580
aactttccca cagataactt ggtttaggtt taattcccaa tgggtcagta tgctcatcta   5640
tatcttgtat taagtattta gtctctatga agttaactat ccttctttga ggattactat   5700
aaggcattgg gctccaatat aaatcataac ccttatactg ttgttcaaag tcctttagtt   5760
ttttgtcaat gttattctta ttatatttaa ttggtacatc tttccattct ttaccttttc   5820
tagctgctag gataatgtaa tctccatttt cacattgttt agagaatata tccttcaaga   5880
actttatgtc catatattat accccctatt ataagtctat attatcccaa cctaattctt   5940
tcaagtatgg aactacttct cctcttggct ttaattttct agtgccttcc tctatctcag   6000
cgaatactaa tccccctata tgtggtttag tcccgttaac tactctcatt atactaacag   6060
ccgatactcc taattgttta gctgcatatc tgaaggatct atactcccta ttattgttgt   6120
aacaatatac tgctttagta taagttgaat ttccacctct tgccatttat acatccccct   6180
ctaacatctg tttctaaaat aagtaaaaaa tttgaggagc aagtttgctc cccttataat   6240
ttgatgagaa ttattcttca tcatcagctt ctaataattc aattatctca gctggtttca   6300
ttttcttatt aacttttatt cctctttctt tagcaagagc aattaagtct ttcttagtca   6360
tttcagagta gtcaggagtt tcattcttca ccttgagctt ctttgattaa agcgattaac   6420
tcatctttat ctttttttctt agctcctttg atacctaagt ctttagccat agcagctaat   6480
tcctttttag ataatgattc taaatcattt tcgtcttctt ctgcttcgtc ttcatcaact   6540
tcttcgaagt cagcatctac tacatcttca tcttccacag cttctatttc tgcttggtat   6600
gcagccttta cagttcctac agccatttct aatgattcta atgcttcctc tacagttatt   6660
tgtccatctg tgtcaggagt tctttcatct aattccacaa tagcttttaa agccttttta   6720
acttctttct catccccaga atttaaagca gattgtacga ttacaattag ctccttattg   6780
tttgcttcct ctaaccattt tgcttttcct tttgccataa taatcattcc tccatatttt   6840
taatttttaa tttttaaata acaaatttag tatagtttga aattaactaa ttataaagtt   6900
ttggttggtg tttgtaattt gattacaata ctataatatc atatcctata tagcctgtca   6960
acgagttatt tagaaaaaat taatttatta taacactcat tacaaacggc ttcatattca   7020
```

-continued

```
acactttcgg gctggttatc aatttgtatc tggttaccct ggtcagtata tttaccttga   7080
tattttaata ttgagaatgt ggctttttta ccacattgac aaatgttctt caattcttca   7140
atgttatggg ccacttgtaa taatctggta cttccttcaa atccttccct tttaaagtca   7200
gttctcaatc cataacatat gataggataa tgtaatgata aatttaacag atcatcaacc   7260
tgttctctgg ataagaattg tacctcatca attaatataa catctactgc ccagtaatta   7320
gcctcaaagt cagaaagtat ttttgataat ttaactctag gaggtagaag aacatccacc   7380
ttccttgcta cccctattct actgattata catggtccac ctttagtatc aattcctggc   7440
ttaaccacta atggcttcat tccccttcct tcatagttat gtgctacctg gattaactga   7500
gtagtctttc cagagttcat agcactatac ctaaaatata atttattgct cacaactgat   7560
cgcctccaat atacaccata ctattacaag tatacctaat atcctaaatg cccataataa   7620
atatcccaag actatcactc ctttgactcc tcccctaaat caaatatacc cggtggtact   7680
aaatccttaa tctctcccat tatggtttca tagttaagtg ttccctttc aatttcctct   7740
gtgtgtttac tcatctcttc cacaaaccta gtcattctag tcttaccata accttccttc   7800
tttagtgtat aacatgataa ggctaacatg atatccacag ctttaagaac attaagattt   7860
ttgttctctc tttcagctct tcttcttgca gctcttgctc ttgacataac aatctactcc   7920
tttatatatt tagtttctaa aaagattgat actactatag ctaatattgc aaatcctagt   7980
tccatttctt cacctcaaaa cctataaaca ctcctagtaa aaatattgat actagggtta   8040
ttaccccctag caccatttac ttctcctccc ataacaagtc agagtaatca gttccttggt   8100
catatgagaa tattaatcct ttttgtgaac tgatataatc agctaagtgt actatcctct   8160
tttgataggt attaattggg tactctcccc attgaccatg atgagactca attagctcaa   8220
ctaccccttt gtatattatt ggaaactctt cctttaatgg ggatagtgtc tctctaacta   8280
gatatggatg ctccttagca ggcttattaa tatcatgtag tattaaagca gctagtatta   8340
tatctctgtc ccttgaacat atcatctcag cttcgcataa tgctttacct atataacaag   8400
cagctttagt atgtcttagc aaacctccta cccctgcact ataagttgga tgatatttcc   8460
cagtactact tgcaggtatt ataaagaact tttcatcaac tagctcattt aaggcctttc   8520
ttacaaaatt ttgtatatct ctatctttta tatcatgaat ttctggtatt agcattctca   8580
tgcccatttc tcttatcata actattcctc ctatcccatg tagtagcctc tatattttat   8640
cttctcccac tcatcaacag taaatactaa tttagttctt tgtggtatgt tagagtaaca   8700
aagataatca aggtctactt ctacatattg tttaccttta gcccaaggtt cattatcaaa   8760
ttcatggtac tctcttacac tgtgtacctt ttttatatag tgctcaagta ggttcatttc   8820
tttctccccc ttttcttctt ctttttctta ctctttccat caagtcctcg tttaacatga   8880
aagtcaagta agttttgagc ccaccttagc atcttaatat cttgcataca tgaaagatta   8940
aagccagtgg atccatcaaa gactttaagg tcattcctaa atggcatact gtttactaaa   9000
cctggattct cattcttaag tttaactacc tctctggcag tctcatccca ttgttggtct   9060
gtccagatat tgttatcata cctataatat attattgaat gaagacaaat ctgtaaccac   9120
ttctttcgta attcaattct ttctggagtt tcttcgcagt catacttgag aattaacata   9180
gcacttcttc tccccaatat tatcacctcc ttttctatta taccatattc ttttaccttc   9240
tacaatagaa aaagtttgac caatatgttc gggttcaatt tcctcaatgg taagtgttcc   9300
cccatgctta catagtatct tagctaatac ttgtcccatg tctgtatctg ctaaagatac   9360
```

-continued

```
cccactattt tttctggtta ttacatacga cttcataact tagccccact ctcaaattta   9420
ttaactgatt atttatctct tgtatttctt ttaacttctt ctcagtcaat cctaagaact   9480
gtcccaattt tatcttctgc tcctttgtta aatgacaata ctgtttctca atcaaatatc   9540
tggcatagtt taggttcttt ctgatctcat cagtattttg cttatgcttt tcctctatcc   9600
cttccagtct cttcaataat gatgtgttta tcatgtgata cctccctaat aagatatttt   9660
gttatctttg gctttctgtc actaaagtcc attactgtgg ctacatcccc atcaatgaat   9720
actactgatt taccaccaaa cttatctttt aagtcatttt tattcttgac tattttacca   9780
ttacataaat acatgatata cctcctttaa aggcctctag cagctcctgt aaggtgtctc   9840
taccacatta taagtaaaat cacattacca catatctaaa aggccttaga attgattgtg   9900
ggctcttata tactgtatct tatgatagct ctattgccaa taacctcata taaatgagta   9960
ttatccttat ataagtatgg atttatcctc atatatagga atacagtact taggtacttg  10020
agatactaat tctccgcaat tcttatctat tgctctagat agaataaatc tgtcctcttc  10080
cattattatg aagaagtcct tgttttcaat gataatttct ttttcattag ataatataac  10140
tttcatcatg gttatccctc ctttactgtc attataagag aagtaagtac aactgtcaac  10200
gttcgggact actgttctct ttccaactgg agaagaactc tctctcaact actgttctct  10260
cttactctct ttccaaccaa acaaaatcaa gagctcgatc gctgaccgtc tgggtttttc  10320
tatatagagc aaaagctcgg aagcatggat atgcctgccg taatgataat ggaggcaagg  10380
caatagcctg ccattgatgt aatcaccatg taatatatat atactatata taataatata  10440
ttattatata gtatatataa tactatgtat atataaaggg ggcataactg atatccctct  10500
acgccagtga taccaatgct tttgtgattt tgtagtttca actgatatgt gggatatcag  10560
actgatatgg ggtaaaaata taggcatatc agatatcagt taatgcctgg actttgacat  10620
atcagtacaa tatatgtata atgtaagcat aggaggtgga tctaatgaag aataactggg  10680
ataggttaca agactacttt aatattgtaa ctactaaaga aagtaaagat ggtaagcccc  10740
taaaaaggga attaaccaat catgaattgt ctgacgcatt cgttaaatta tatattgaag  10800
tatctaaaat gaagagagag aatacccaat taaggaataa tatcagagca atggatggtc  10860
atcctgtaat ccagattaac gatccgaatg ctaaattaga tgatatttcc ttgtatttat  10920
atctaaaaga cttctggcca agtatatttg aggactataa agccaagatc cagagtagta  10980
agatactaaa aggcaagaga tttaagtcat ttaaagaggc taatgattat gtgtggaagg  11040
atctaatcca gaatagtaaa gtaaagaaga ccaatgaaag tctatttgta ttaagtaaat  11100
gggtagatgg tatgggtatc aagcataatt tcaggaataa gcaagagttt gttactgctt  11160
gtctgtgcta tatggactat aaaggatatc tggacaagga gggtaagacc tttaataagc  11220
taggtgatat taagagagga agcttcagat ttaattctga tgaggaaacc tatgcaatac  11280
taactgatac ttttgatact gtgggtaaat ataaatctgg aattgagaaa ttcaaattaa  11340
aaataaagga gttaaaagag aatgattaaa agaattatgt cattactaac aataattgtg  11400
ataggagggc tactgttaac catacagagc ctaaaaaagt aaaaccaaag ccagcccaat  11460
gtattgatct ggattatggt gatatacctt tctaaagttt ctcttgacat atgatagga   11520
atattatata ataaaattga ggtgataaac tatggaaaat aataacaaca gaataagcag  11580
agaaacactt tacatggaag ttgctaaact tatgacagga agatctactt gcctaagaaa  11640
agcagttggt tgtgtattag ttagagataa caggatagtt gctacttcct ataatggagt  11700
accttcagga gtagaacatt gtaaaacttg tttaggacct ggatgtgata ttgtgatcca  11760
```

tgcagaagct ggcttaataa gttactgtgc taaacatggg atctcaactg aaggaactac 11820
tatgtatgta accttatccc catgtgagag ctgtgctaac ttaataatca atgcaggaat 11880
taagaaagtg gtatatcttg agaaatacag attaagtggg ggaatagcta aattaatttg 11940
taatgatgtg gaggtagaac aatatgagta aaggaaaatt ctttagtgat agtcaattaa 12000
aggccataag agctatggcc tctgcaggta ttgaggaaat taaaaatccc tatgaaagta 12060
acattgatga gtttgataga ttatcagaag aaaaatatat cagagaaaaa ttattgtggg 12120
aagaaagccc aaggattaag ccagttccag ttaaaggatt ggaagaagtt aaagaattta 12180
tagatggact agatactgaa tgtgaagtat ttcctgtact aggaactaat aatatagttg 12240
tgatagaacc tttagtagga gtagatctag tacatgataa agtaagagaa gcatttcaag 12300
gatgtaacat ttccagagta tcaagagcaa tatttattac atttaaggag gataataaca 12360
atgagtaaat taatatgtaa aagaagatgt tatagaaggg atccagcagg taactgctta 12420
gcatatacaa ttccatatgg gccaggagaa aaatgcccta gccaatgtaa taatccacat 12480
caattaaaga aggagtgtca agacatcatt tctaaaaatc aacctaacaa tccaatagta 12540
aaagaatgtc tttacttgat agagaagatg gatctaataa ttggggttga gattaataaa 12600
gcttatgagg aagataagaa tagaggttca ggtggaggat ctaagaactg taaacctaat 12660
acagcagctc taaagcaaaa gatgaaagat aatagaccta ttgaatgtaa acaaactaaa 12720
gaggagaata aggaatatca ggaagaatta aaacactggc aagaagacca taatgaaaaa 12780
ctagaagttc ataaatcagt tggatatggt atgaacaggg gtaaggtaga ctcatatact 12840
ggtatagaac ttgatactaa aggtaatcca gtatattccc cagaagaaat acaaattgca 12900
gctgataacc tgctacagga aggaagaata gatgtggata tgtatgaaaa aatattgaca 12960
ggtgaaataa aattataaaa cgttgacata attaatccag atgtggtata atagtggtat 13020
aaatccatag ttaattttgc catttggttg gtattactag cattaaggtt agtgtgccaa 13080
ccatttttca cgtagtaaag tctggatttt aagggggtga tattgtatta tgagctataa 13140
gtcatacact gaaccagagt actgtactcc tgaacattcg aagaaagcca aaaaattgat 13200
atataatgcc ctgaaggctg atccctttac acatcctaaa caattaagaa accttgctaa 13260
ggtatcacag acctttgtta ggcagtgtct aagagagttt aaagagcagg gcataacatt 13320
tttagaagaa gaaggtgata ttgtggcatt gagtagcaaa acaaaaaaga ctattaagac 13380
cttggctgag aagtatgatc ttgatgagaa agaagagttg tttgtatttc attacatgaa 13440
gtgctttaat gcaactacag cagctgctag ggcaggctat cctgtgaata attctcatgc 13500
acatgggtct aaactattaa agaagaagaa aatacaggaa gctctaaagg ctatcagagc 13560
cgatagagat gaagaattac tatgcgatgg tatggatgta ataaggcagt acatgaaaat 13620
agcctttgca gatataactg atgtgtgcca attcaaggat gacctagttc tattaaggtc 13680
tagtaaggct gtagatggta ctctaatcaa tgagattaaa caaagtaaag acggcgtatc 13740
agttaaaatg gaagatagac ttcaggcact aaaaagactt gaggtatact tcggcttaag 13800
tactgatgtg atgaaagttg aacttgaaaa agttaaatta cttttacaaa tacaggaaaa 13860
tcagaataat gctggtaagg gaaaagatct tgaggttctt agagctaaaa tggctgatag 13920
aaagaaaaag aatgctaagg gaaggaagag tgaataatta tgaatgaaac tgaatttacc 13980
atgattaata gccttcctct ggaggttaag gttagaaaaa ctatgttaag agtacaagaa 14040
tgggtagacc attttggtga agatggagta tatatctcct gtagtggggg taaagatagt 14100

-continued

```
ttagtattag tttatatcat taggaaactt atgggactaa agaatatacc tattgtttat  14160
gtggatagtg gcttagagta ccctgatgta agagaaaacc tattaagaga atatcctgat  14220
gtagtgatta ttaggcctga aatgaagcct aaggatatta taaagaagta tggctatcct  14280
gttatatcca aagctaatgc gtctatatta tacaaactga acaactataa actaaagcca  14340
gaatacagag acaaattatt gaatgggaat gaaaaaggta aggtaggtac actgcctaag  14400
aaatatcata gcctgattgg atgtgaagtt caaataggaa aaggttgctg taatgttata  14460
aagaaaagaa ctttccatag atatgagaaa gaaacaggaa gagtaccatt cacaggagaa  14520
ttagctgtag aaagtaatct tagaaagaag gcttatctag cagaaggatg taatgccttt  14580
caaaggaaat taggacctaa atctatgcca ttaggttttt ggaataccaa tgacgtacta  14640
actatgtgta agaagtacaa tatcaaaata cctaaagtat acggagatat aattgaggac  14700
tacacagatg agaatggaca agttatttat aaaacaactg ctctaagtag aacaggatgt  14760
acttggtgtg gctttggtgc tgaatttgat gataggttta taaggctaaa ggaagtccag  14820
cctagaatgt atgattatat tattaatggt ggagatttta atgacctagg ctattgggag  14880
cctaatgaag aaggtttagg tttaggatat gtactagata agctaggaat aaaatattag  14940
gggggaaggc ctatgtttga tttagataga atgattgaaa aattagagct agatgcttta  15000
gttgataagt tccacatcaa caaggaagcc ctagaagaaa tatcctttga agaattagta  15060
gatctatatt atgacgatcc ttgtggattc tcagaagata tattaggagt acaattagat  15120
ccacatcaaa aggatatttt aataagtgta agagataata agagaacctc tgtaaggtca  15180
ggacaggggg taggtaagac tatggcctgt gcttgcctta taatttggta tatgaccttt  15240
aggcctgaat gtaaggtaat tgctacagct cctacatttt cacagttaac atctgtatta  15300
tggcctgaga tatcaaaatg gctacaggga actattgtgg aggattattt tacagtaaat  15360
aaaactacta tgactaggaa ttgtagtcct atgacttggt ttgctatgtg taaaactagt  15420
aatagaaaag agaatatgct tggtcttcat agtgagttca tgctaattat atgtgatgag  15480
gctcctggaa tagatgatga gatcctagaa gcattacttg gtactatatc agatgaggaa  15540
aataagataa ttttgattgg taaccctgtt aaaaatacag gtatcttctt tgattctcac  15600
cacagtctta aggaaaattt taaatgtatt catattgacg ctacaaaagt tgatagaact  15660
gataaagaaa accacaaaat gttaaggaaa aagtatgggg aagagtccaa tgtctacaga  15720
tgtctggtaa aaggggactt ccccttagaa gaagatgaca tatttataca attatccaca  15780
gtatatagag gtatcaacag tgaaataacc agacctacag aaccagttac catagatatg  15840
ggtgtagacg tagctagatt tggttcagat aagacctcaa tcatgaccaa aatcgatgga  15900
tatgtggaag aacctatcta ttatcaaggt aaggacacca tgaaaacagt gggagaagtg  15960
ctaaggaagg ctaaatccct acatggtgag ttccccaaac tagctgtagt tgtgaaaata  16020
gacgacactg gtgtaggtgg gggagtaact gatagattaa aagagataaa acttgaagaa  16080
aaactggact ggttgaaggt agtaccatgt aagtttggta tgccactaaa gagagggtcc  16140
caggcttatg ccttttatta tgatacaacc acatatatag cctctgtagt taaggaatta  16200
ctggaggatg atgagttaag actaccagat aatacagatc ttgtgggaga attgactacc  16260
agaaagttta aagtattcaa ctccaaaggt caaataaagc tggagagtaa ggatgaaatg  16320
aagaaaagag gactacattc tccagactta gcagactctc tattcttagc ttgccttcct  16380
gttggatcta aattaagaaa aatctagtaa ctgatatgcc tattaaagcc aataattttt  16440
attctgatat gtgagatatc agttttgaaa ttgactaggc tctatattag taataatgtg  16500
```

atatagaagg catatcagaa ttaccacctt tatatatatg taatataagt atactatata 16560
ctatataatt tatttcataa attaatatag taatatagta tacattaata attatataat 16620
attatatggg gaatatatgc ggaaaatctt ccggaaaata atataaaaat aaaacgttga 16680
caaatttttg tgagttatgt tataataaac gtatcaaatt atagttattt ttaaatcatg 16740
tgaatggccg tatttgacac tatatgtgga gttgatgtag tcctccctga aatatgaggc 16800
catctggatt ttataatttg atatataatg taagaaagga ggtaaagtaa ctttgaaaaa 16860
gatatccgcc agaagtatat gtggagaccc tatccaaaag tctttggatc cagtggataa 16920
atccaatcaa caaaccagtg tacttggaat tgaagttgat gagatatccc ctgactatga 16980
cccccaacta ttagaagtga ttataaggga gtctacaata ataccccaat gcaaaaagac 17040
ctaccgaaat aatattgctg gattcggaat aggtattagg tatattgaga aggtagatga 17100
acctactcca gaaatggaag ctgaatataa acagctggaa gaattaattg ataccctgtc 17160
ttttgataaa ccaaccaaga atgtctttga agagatagtt gattggagag aaggacttgg 17220
gtattctttt ttagagatcg tagaagatcc taaagaccca gctctcgtaa aagagataaa 17280
agaaattgaa gaccctaaga caattaaaat tcttaagcta gatgatgaga gtaccgagta 17340
cactgtaacc agatatggta aacagtacac tagaagaaaa aggttcagaa gatttaagca 17400
gactgtaaat aatcaatcaa tcttctttaa ggaatgggga gatcctagag atctagatat 17460
gaatactgga aagtattatg aaaagggaga gatacccctt aaagatcgag ctaacagtat 17520
acttcatttt aaaacaggtt atggtgttta tggtacacca agatgggaag gtcctatgtt 17580
agccgctcag ggttcaagaa aggccgaatt attaaactgg agatatttta ctaatggtaa 17640
acatactcca ttaatgttac taattcaagg tggtactctt aatgataaat cttggaatga 17700
attaactgag tacatgaata gtgtaaaagg tgaaaattcc cagcatggtt tcttagtatt 17760
agaaactgaa gctgcagaga aagacactgc ccttgatgac tctaagccag ttactgttga 17820
ggtcaagccc ctatctgaaa tattacagaa ggatgagtta ttccaagact acatggataa 17880
tactaggaaa aagatacaat cttctttctt actaccagat atatatgtag ggtactccca 17940
agattataat gtggctacag ccagagaggc tacaagaaaa actgaagagc aagtatttgt 18000
tcctgaaaga gaaaacctaa catggatact aaataatgtt attctatctg gctatggttt 18060
taaatatgtg gaagcttact ttaagagtcc taatattgag aactctgatt atcagaaagg 18120
aatgtttgct atagcctcta gagctatgac tcctaatcag attaatgagg agtattattc 18180
atcaatcaat aaggactata ctcctattga tgaagaatgg gcaaatatcc ctacttactc 18240
agttgcctct tctatgagta ataacttaac aagtataatt gagaaggctc aaaactccaa 18300
tgggagtgat gaggtgatag ctgtacttaa agaggctaag aaacagttat taaactatca 18360
attaaaagga ggtaagcaat agtgggtact gatgagttga tcgctaaaat tgataagatc 18420
ttaaagaatg aagatgatag ccttaagaaa gaattgaaag aagctggcta tgaggagatt 18480
gattatacaa tagaaaagat ctctgaatta gaagacacta tttctgatct ccttacagaa 18540
gaattaaaac atcttataaa agatggagac tttgaaacca ttgaagaatt tatggaatat 18600
gtggagtctc aaataggtac agataatatc gatacttctt tagcagaaac tcttaagagt 18660
tgttatcaag aagctataga aaatttagga gatacttatt tacaaggtat tgataaggac 18720
ttatccctaa ccaaagtctt ttctccatat actactacct ttatagatga gtggtcttct 18780
aaacttgggg aaatgatgaa attaacttcc catgaaaaac tacagaatat tctggataag 18840

-continued

```
gctcttgaag atggagagtc tgtagaagat gtagttggta aattatctga gacttatggc  18900
tttagtagaa ctagagctag agctactgct attactgaaa tgttaagagc ccactcatat  18960
gctaaggatg aggcttttaa tcaatgcccc gcagtaacag gaatacagtg gaaacactca  19020
gggggaaggg gtattcaccc aaggcaacac catgtcgatc tggatggtac tgtcattaat  19080
aaaggtgagt acttcactgt aggaatttat gaagctagat ttcctagaga tatcaactta  19140
cccgcttctg agactgtgaa ttgtcattgt actcatgggc ctgtaattga taaggatata  19200
ctaggattat ctaaagaaga aaaagaagct atcagagatc aagtgatagc agaatataat  19260
ttgtaaagga gggagagtaa atgccagtaa aatcagttaa gaaagctatt gagatctcag  19320
atgctaaaat tgattacctt tcattagttg ataaagcagc taataaatgg caatggattg  19380
tggctaaaga acttggagct cctaatagat ttagatatga taagccaatc ttaaagtctg  19440
agtctgaagg agataatcat tttgttattg gtgtagtata tgagccaatg actgctgact  19500
accatgataa ctttatgact gaggaagaga tcaaaaaagc ttgtgagtgg tttaatgaaa  19560
atggccttgg tagtgattta caacacaatg agaacactct tgagggtgtc aagattgtaa  19620
aatcatgggt aactgaggaa gataccacaa tagaaggtac agtagttaaa gctggaactt  19680
ggttagctaa agctgagatt atcgatgatg atctatggag caagattgag aaaggcgaaa  19740
ttactggatg gtctatgggt ggtactggta aatattctac acaagatgta gatattgatg  19800
agattgagaa gtctataggt caatctatac ttgataaaat tggaaaggcc ctagggttaa  19860
ctccaaagca tatacagaaa ggtgcatact ctgaaaaata taaagagact gcaaaaagaa  19920
ataatttctg gaatgcagtt agtaccttag aagatattct atatccatat tctagttggg  19980
attacactag atcttttgaa agtgatgtag ataagataaa ggaggctctt caagaatttt  20040
ctgaaactat ggagggaata ttattaggaa ctccagaaga agtagctaaa tcttttgagt  20100
taccagtcaa taaggcaggt aagaaaatat cttcaaaaaa tgtggaaaag ttaaaaacag  20160
cacaaagtgc tattaatgaa ttattagact cagtggaggg ggaagaagag atgaatgaaa  20220
ctcaagtaca aaaaatgata gacgaagcta tcaaaaaggc attagatgga actaaacctg  20280
ttgagggtga agttaataag aatgaaggtc aacaagctac tactgaagat atagttgcta  20340
aggctgtgga aaaagctatg ttagaggctg gcttaatcca gaaacaagaa gaaaaaactg  20400
aggaagaaaa aatagctgag gcagtagcta aagccatggc tccatatgta ggaagtaaac  20460
aaattgctaa aaacggagaa gaaggacaag aagttcaaaa atcagtattt aatggattat  20520
ttggtggaaa ccaagaataa taacaattag gagggaaagt tatgtcaaaa gtaaataaag  20580
ctgtatttaa cgctgccgta ttaaatggtg gaggtaaatt aaatccagaa caagctaacg  20640
cttttattaa aatgataatt gatgagccaa caatattaaa agaggctaga actgtaccaa  20700
tgaaaggaga ctctaaaaag attgagtcaa taggatttgg tcaaagagta ttaaatcctg  20760
cagctgaagg aacagatcca ggacaatcta aatattcagc tccaactact ggaacagtta  20820
ctttacaagc taaagagttt atagctgtgg ttaagttaac tgatgatact atagaaacaa  20880
atatagaagg aaaatcaata gaagacactg taatgcaatt attagctgag agagttgctc  20940
ttgacatgga agaaataatt gtaaatggtg atactggaca tagtagcgat actttcttac  21000
aacaattaga tggggttaga aaacaattaa ctgctcatgt agtagatgct aacaaagctg  21060
ctttaagtaa agacctatta aaacaagcta agaaagctgt accagctaag tatttaagaa  21120
acccaggtga atggagattc tactgctcaa atggtttaga aactgattgg gtagacttag  21180
taggagaaag attaactgct aatggggatg actcatttat aaatggtact gttaaatctg  21240
```

-continued

```
cttatggagt acctgttaaa ggtatagcta tgctacaaga ttatgacgac tcttctactc  21300
aagtatcaga cataatctta actcacccta agaatatagt tataggtatc tcaagagata  21360
tcagaataga gttggaaaga gctcctagag aaagatctac ttatgtagtt ttaactctta  21420
agatggatgt taagtttgaa gatcctaaag ctgctgctaa gatagttaaa gtaaaagctt  21480
aatcatgaag gcccactgta aatgtgggct ctttttcatt agaaaggaga gatattatgg  21540
ctaaggtcaa attagcaaag ggtaaattac aaactctggt tattaagggt catagaatta  21600
cccaagacca tgtagaagaa gttaaagata gtctagtaaa ttatttaaaa cagaactatg  21660
atgtgattgt catagatgaa cctgttgagg atgaacctct agaagatttt actgaagaag  21720
aagtaccttc tacagatgac aataaagaag aacctgctag aagatttaca aacaagaata  21780
aaaatagaaa cagatagggg tggctcatat gaatattact ccggatgaaa taattgactt  21840
ttcaagtaat cctgagatta agaaaagaga ccccaaaaat attgagatgg atatattaag  21900
agctaaagct aagatctcag gaatttttaa aaattcaaat aaagactatg atactattgt  21960
ggagaaaaat cccaatagta aagaattaag attagctcat atactgtatg ctgagtatta  22020
tggactacaa tccttggtca ttagcaaggc tgatattcaa tccgagacct atgatgacta  22080
ctcatataca agaagaactg ataaggctgt tatagagcct gatattatgc ctctgattaa  22140
acctttctta gaagatgata gtccatctat cagaacaact actatgagat taagggtact  22200
gtaatatgat tagaaattca tataacaagc tcttaaatca tagatgtaat atataccacc  22260
tattggaaga ccctgaagat cctggatatg gcctagccca taccccctagc tttagttatc  22320
ctgatgagcc agacatgatt gaggtaccct gtcattttaa atcaggaact ctagaaaaac  22380
ttgagtacaa agaacccagg tttaagatta cccaggagta ctcagtagat tttgctattg  22440
gaactgatgt tagacaaaat gataaaattg tggaccttga gactggtatc acatatatag  22500
ctaaagctcc tagggatata agaggtctaa aaattaaggt tggtatagag gctaaggatt  22560
ttagatagtt atggcttcaa attctggagg catagaaata gatgctaaac aaatagaaag  22620
gtttataaag aagctaagag atgccgctaa tagtgatttc aaaaagcaat tagcagtatg  22680
gtttgaggct gcagggatag acttccttga tgtggttcaa gatgaaataa ttagactaca  22740
agtagtagac actagattat tacttaactc ctttcaaaaa gggggtaaga atggtatatg  22800
ggtaagtagt gatggaggac taaccttaga agttggtact aacctaaaat atgctaagtg  22860
ggtaaacgat ggtcactata ctaatccaca aggacaatca tttagattcg ttcctggcat  22920
atggtcagga gataaattta tttatcaacc aggagctaag actggtatgg tactaagaca  22980
aaagaaagta cctggtaaac cttattggga caatgcagta aaaatatatg aaaaagtatt  23040
tgaacaggct ttccaaagaa aactagaaga ttggttagcc gaagttttag gggtagttta  23100
ttaatgacag cagatatagg gagtattgct aaattcatat ctgatctaac tggaattact  23160
accctctatt ttgagcgaat acctgaaaag ttcaagtatc cctcattata tttcaagaag  23220
gtatttaatc ctcagaatga tactctttgt agttatagaa ctgagaatac tttaagagtt  23280
aaggtatttg aacctaagga ctctcttgaa attgctcaga atatagctaa tgctatatac  23340
ttgagaaata gaaaaattcc catacttaat agggatggta gtaagaccaa caaaaatctc  23400
aaaataaaga atgtggaagt atttgaaggt gaaactgaag aagattctca ggtagagata  23460
aactatgata ttgtggttag tctttataaa gatccaactt acttcgaaaa ctttgagata  23520
acaaaggggg taaaatagtg aaagtacaaa aattttccat acctcaatta agagcccatt  23580
```

-continued

```
gtcaacaact tttccaggtt gaggagtttg tcttcaacgc tgcagttcaa tcccttccac  23640
ctgatgaaga gttaacaata aaacaaacta gtcagattat aaaagactgg ctaaagaagg  23700
aggtaaaata gatggcagga ggaactttta ttccaggaca aaataaagta agacctggta  23760
tgtatactag atttgtaagt ggtggactta atgagcctaa gcttaataat ctaggagtta  23820
tgatcttacc attacaactt aagtggggta atgctggaga tgttatcaag gtaaccaatg  23880
aaggtggcct agaagcatta tatcaacttg ggtatgacat aactcaccct actgtattac  23940
tggttaaaga ggctttaaaa gaagctgcaa ctgttttagt atataaccta acaggtggaa  24000
ctaaagccaa agctgtagta gggtctctaa catttacagc tactaaagct ggagaaaggg  24060
gtaataaatt atctctaact attaagacca atcctcttgg aggaaaggat atattattat  24120
atcttgaggg gtctaaaatc tttgaggcta caggagtaac tgaaatatca acagttaagt  24180
ctcaatggtt tacagtaagt ggaagtggct ctatagatga gactgctaag actgagttta  24240
gtactggtac ttctactcag atgaataact ctgatgttat taacttctta gataactgtg  24300
agttatacaa ctttaaaact atggccttcc catttactga tagtgaatta cacactgctc  24360
tattatcaaa acttaaatac ttcagagatg aagttggtaa gaatattgtg gcagttactt  24420
ccgactttgc tacttgtgat tacccatata tcatcaatgt taagaatggg gttgtattag  24480
agggaggcac taatttaaca gcttctcaag caactgcatg ggtagctggt gctagagctg  24540
cagctggata tactgaagac cttacttata aagcatatcc tggagcagta gatgctaatc  24600
caagactaaa acactctcaa atagttgatg gattaaaaac aggtcaattt atattctcaa  24660
ctcaaactga ctcaaattct gaaagagtaa aggtagtagt tgaggaagat ataaatacac  24720
accatacttt tacggaagag tgggatgaaa gctttacaga taataaagtt gtggctgtat  24780
tagatgctgt tatagatcta ggatctcaga tcttagttcc taatgttttc cctaaccaca  24840
aagatggtat aaagctagct caggatagac taataagttt attaactaca ctacaagctc  24900
aaggagcctt aaagaatgtg gatcctgact ctgatgtagt ggtagatgaa gaagctagta  24960
aaggaaagac tatgtatgct actatactta cacaacctgt aagaactttc aagaaatact  25020
ttgtaactgt taagaataat taaggaggta tagcccatga gtgaagttaa tagaatgtct  25080
gctagagagg gtagagcttt tgtatcaggt aagcaagtaa ctagcttaat aaaactagaa  25140
gctctattta ctcctgaggt gactaagaaa agggttatgg gtcagaaagg attaacctca  25200
aaagttatag gttatgatat aactggaact ataactcaat tcaaagctac tccaatgata  25260
agagaagcta ttaaagaata cttaaaaact ggtatattcc ctaagatgga tatacaagct  25320
gtatgtgatg atccagattc tgactatgtt aagaattatg gtgaggacag agtacaatta  25380
ctaggagtac aattagaagg agatttacca ctaattggac tagatgctga gggggaagaa  25440
attcaagaag aaatatcatt ctcagcttca gaagtaagat atttataaaa gattaagaat  25500
attgtggagg tagattatta tgtcaaaatt tagtatggaa tttttcatgg aaaatgataa  25560
gggtaaacaa tcacccgaaa ttgaagttga aggggtagct agatttagtt tccctgaggg  25620
tcatgaatta gcgggccaac ctataccttg gatattaaag ccaatcacta ctaagcaaat  25680
ggaggatatc caaaagagaa atacagtaat tactagaaac aagggtataa ctaactcaat  25740
aacagaccaa agaagagcta ctagggaaat gatactagaa acaatagtat tccctgactt  25800
taaagatcca aaatggttag agtctactaa gtttgtggat ccagtagatt tacttatgga  25860
tgtactaagc ttaccaggag atttcactag aataactagt gaggttatgg atataaatgg  25920
attaggcgat aataaggatg atctaatcaa agaagcaaaa aactaataaa ggccgacact  25980
```

agtgcatttt gggctcatgt gttattccag aagcataata tactaccctg ggaatttgat 26040
aaactatctc ccaataggaa agcctttctt atagcttcat gtgaactggc tttagaagaa 26100
gataaaaaag ctagggataa gttaaagaaa ggctcttaat cataaaggag ggatataatg 26160
gcaagtcaag ctgcatttac tgccatattc tctgcccaag ataagatctc tggtgcattt 26220
aaccagatgg ctgatagtgg taattccttc atgggtactc ttgccaaaat tggtggagta 26280
gctgctggag tattctcagc taaggctgtc tgggatttta ctaaggacag tgttaaagcc 26340
tttggggatt ttgagcaagg tttaaatgag gttatgactc tattacccaa ctctactcaa 26400
gagacctttg ataagatgtc cggccaggta aaaaaattaa gttctgatat agggatattg 26460
cctgataaag tagtacctgc tctttatcaa gccatatcct catcagttcc agaggataac 26520
gtttttagtt tcttagaaac agctggtaaa gcttctatag gtggtatcac atcaatagaa 26580
actgcggttg atggactaac tactgttatt aactcatatg gagctaagaa tatggatgtt 26640
caaagggcct cagaccttat gtttactaca gtaagacttg gtaagactaa ctttgagcaa 26700
ctatcacaat ccctattcaa tgtgctacct tcagcctcag ctgctggggt atcttttgaa 26760
gaagtatctg cctctatagc tgcattaaca gctcaggggg ttccaacatc tgtagctact 26820
actaagataa gagctgctat agatgagcta tctaaatcgg gaactaagac tgataaggtc 26880
ttccgggaaa tagctggtaa gggtttcaaa gacttcatta aaggtggagg taatatccaa 26940
gaggcccttc agatgttaga aaaacacgcc cagaaaagta atctgggtat caatgacctc 27000
tttggttctg tagaagctgg ttcagctgca ctagccttga ctggtgaagg taccgaggcc 27060
tttactaatg ctcttaatga gatgaagaat agtgcggggg ccactgaagc tgcctatgaa 27120
aaaatggata agggctttaa tagaaccatg gagagaataa aatccaaagc tgctgtagtt 27180
atgttagatg tgggagatgc cctagcccct gccgttgagg ttatagctaa tgctgtccta 27240
aatggtatca catttataca agaaggcttt gaaaaactag gacctatatt ctcaatggtt 27300
gtttctgctt tccaaggttt aggagagact atatattaca tcatgaatgg ttgggagttt 27360
ggggatgcta tgcaaccctt tatagatcta accaatgata tattatataa gttcttacct 27420
gctgatgtgg cagatcaaat taatgagaag atatggagtc ttggagaaga catatataat 27480
aattttggag agatcttagt aggtctacca gattatttat cagaggctaa caataatata 27540
caagaagcct ttagtggttt agctgagcct atcatgggag tattagctcc tataggtcaa 27600
gtacttcttg atatgtttgg aactttagct tctatattta tgaataacct aattccagcc 27660
atagacttag tagttcttta tgttcaagga tttactcaag tatggcaaac tgtattggaa 27720
gtgttaggtc ctatattaga agtattaggt tctatgttct ctgctacttt tacagctctt 27780
ggagaattga taaccaatgt tttcatgcca attgctactt ctttagctga ggcctttgct 27840
acttatatag ctcctgcaat ttctcaagtt gtggaagcta taggtaactt cctaatgcca 27900
atattacaag gactagcaga ttggtggaat aatacactac tacctatgtt cttaagcttt 27960
gctgagaatg tagttccata tattcaatca gctattgaga gttttggtat gatattccaa 28020
gggttggtgg gtatgctaac tccactactt aacctttag ccgcatcttt ccaaacagta 28080
tggcctgtta tatcctcagt tgttactggg gccgttcaaa ctatatcagg agtactacag 28140
ggattaatgc agatgttgag tggtttaata gcttttgtgg ctggagtatt caccggtaat 28200
tggtctaaag cttgggaagg tgttaagaac atctttgggg gtattttcca aggtatgtta 28260
tccctagcaa aagctcctat taatagtatt attggtatga ttaataacct aattggtgct 28320

-continued

```
cttaatacta tcaagatacc tgactgggta cctattattg gaggtaaggg tattaatatt  28380
ccccagatac caatgcttgc tgaaggtact gacttcttta cagataaagc tgccatggtt  28440
ggtgaagctg gtcctgaatt agttatgggt cctacattct caaaaatgcc tagaggctct  28500
caagtattac ctgcagataa aactcaggat ttactaagac aatctggagc aggaagtgat  28560
gatggatcta aagttatgaa cattaacaac tcatttaatt tcacagtaca ggctgaagat  28620
ggaacaatct cagaaagtga attaatgaga gtatacagat ttattgtgga aatgttaaat  28680
caggaaatgt tcgagggagg tgaactggac cttgcatagt aaatatcaat tctggttaat  28740
acagggagat actaggttta ggttaccagt aaatcccact gatataaata tctctgatag  28800
tagagataat agtacagttt ccattgaagg cttaggggaa ctctctttca taggagaccc  28860
taagctaaaa tctttttctt ttaattttga gttaccaagc tcctactacg atggatgtga  28920
gtatactgat attgcagacc ctagagtaag ttatgctaaa cttattgaaa tgggtaaaga  28980
tccagtaaga tttactatta ctagtactga tattaactta ttagttacta ttgataatat  29040
ctcatatact gagaaaggtg gagatattgg tactcttcaa gtaaaaataa aactaactga  29100
gtataagaag cctgaggtta aatcagttag tttcacaatt ccaaaaccta aactagccta  29160
tagtggtaat acaggaggta gttcttctgg aggtactcaa ccttgggcag ctactactac  29220
taatgtttac tcatggctat gggtaagaac tggacctggt atcaataatc ctactaaggg  29280
taagatatgg cctaatgaac actttacagt attaaggtct caaaatggat ggcattatgt  29340
aaagtataaa ttagataatg gttcaggata taaagaaggt tggagttctg gtgattatat  29400
aaggaggtta taatatgcaa ttaattgtgg tacaaggaga taaatccttt gatattacaa  29460
atacctccag tggtaagagt tgggcagggt cttcttcatc tgcccctcgt accctatcat  29520
tccaatataa tgctcaagat atacatccaa tttatgatgg agatcaggta gtactagtcc  29580
atgagggtaa gaatatcttt aatggtatta ttatgaatat ctcagataat gagaaaaagc  29640
atttacttaa ggttaaagct tatgacccta tgatttattg ggctaataat aaagatagct  29700
ttgtattcga aaaccaaact ggcgaagcta tatttgagtc attatgtaaa gcctttgggg  29760
ttgcccctgg agtagtagct aaaactggat atactttctc tagtttagta tgtgagaaac  29820
aaactcccta tgatattatg aagaaggtaa taaaagaggt ttatgaacaa actggagaac  29880
agttttatat ttattataat tctattacag gtaagtttga ttttataaac cgaagaacca  29940
ataatgaatt gtggaaattc gaatatggta aaaatattgg aacttttttca agaagtagaa  30000
actttgatag tattgtcaac caggtaaagc tagtatgtaa atataaacag ggtaagggta  30060
aagatgatcc cgagattact ttatttgcct ctgctaaaga tgatagcagc caaaagaaat  30120
atggtgtatt tcaattatac gatactatca gtgatgaact aaaccaagcc caattaaatg  30180
agaaggctag aataaagcta gaaacaggta agagacctaa aactgatatc tctataactg  30240
ttataggtgt acctgactgt attagtggta aagccattgt ggttagtata ccacatttaa  30300
aaattaataa gtctttctac attgagtctg atactcataa atttgatact gactacacca  30360
tgaacttaaa acttaaatgt actgaggagg gtgatattta atggctaata atttattaga  30420
ctgtgtaaaa caagtatata gtaatatgtc cacccctcta aatatttata gggctaaggt  30480
acttagtact agccctctaa aatgtgagtg tcttcacaat agaaaattag tactatctgg  30540
aaatattata gatgttccaa aacatattga gtctattagt gagggcgata ctgtttatct  30600
tatgccttat gatgatggac aaagatattt tatgttaggg atcttaggag gttgatataa  30660
tgctacctaa tggctttaaa gataccctta tagttgatga gaaaacaatg gagaatacca  30720
```

```
agacctataa actggatcta aatcttaata ggatttatga taatgtggat ggtcttgagg  30780
ccttaaaaca atctttatat aaaagattaa taactcctaa aaatgcctat atgatttatc  30840
aagatacttc ttatggttgt gatattagag ctttgattaa tgactctcta gtaactcctg  30900
aacttcttga aatggagatt aatagggcta tccctgaatg tctcttagaa gatgatagag  30960
tgactaaagt aactgatcta aagtataatg tgcaaggtaa gaatgtatat attgaagtat  31020
ggataaatac catatatgga gatacaaaac tggaaggggt gatataatgg gattttctga  31080
agatttattc tcccgaacac ataaagaatt actagaagaa atgataggcc tatcccctga  31140
tgatattgac actaggactg gaagtttcac ctatgatatg gctatggttt ttgctgttaa  31200
gctagctgag ttctatgctg ttaatgttaa ccaaatatta gactcagcat ttctaagtac  31260
tgctacaggt aagttcttag atgagagagc tgccaatgta gggatatcca gaataattcc  31320
aactaaatgt agaaggtcag ctaaatttgt tggctatgaa cccgatgttg gttcaagatt  31380
ccaaggggga gattatttct ggcaagtgat agagcccaat attattgaat gtgagaccct  31440
aggttcagga cctaataaag tatcaacagg tacacatcta attcctatca atgccatagc  31500
agagcttagg agtgctacta tgggagatat acttgttatt ggtagagatc aggagacaga  31560
tgatgagtta agagaaagag ctactaaagc cactatacaa ccatcgggag atggaaatgt  31620
tcaacagtta actgattggt gtaaaagtgt agctggagtg ggtaaagctg tggttcttcc  31680
ctgttgggat ggaataaata ctgctaaagg tattataacc acagttgaaa ataagcctgc  31740
taatcctgag ctagttaata aagttcaaga atacatggat ccaggcaaga aaggtttagg  31800
tgagggtaaa gctcctatag gatgtgtttt tactgttgag tcagcccaaa cctttaatat  31860
cactgtaagg gctcaggtta agaaattgag ttcagttaca gaagaacaaa taaaattaaa  31920
cttcaagaaa gaactagaag agtttctaag cagtcaagta tttaaaatta ctagcctatc  31980
tataaataga ataggggcta tgcttttaaa tattgaggga gtagaagatt atacaaccat  32040
tacacttaat ggaagtagtc aatctttaac tattcctgct aaccaaatac caaccattac  32100
tgaggtggtg gtaacttatg tatagtctag aacaggttca aaaagaatta ctattgtatg  32160
ttcctgaatt ttatgataat ataaaagagg ctgataactt agtaaacact attatggcta  32220
ctgaacttca gaagctatat actaagggac aggaattaca agactatgtg gatcccaaga  32280
ccactcccaa ggaaggacta gaaaggtttt tcactgatct tgaattatat aaatactttg  32340
attacccacc aactgaccaa gagaaaagag ctattattac agtagttcta tctgcttgga  32400
aaaagtttaa tagtacatct atcaaaaatc ttactaaggc ctatacaggg ggaaaggtaa  32460
aggtagagtt catagctgaa gagagtaaga tcaaaattag ctttactgac ctacccgggg  32520
taccacctaa tctaaaggcc ttagaaaggg tattcaggga aagaatgcct gctcatttaa  32580
tatatcaaat tatattactt tatattactt gggagatgtt cgatagatat gattatatgt  32640
ggagcaagtg ggacagtcta gaccttacct gggaaaaatg ggaagaatat gctataactg  32700
aataaaggag gtatgcaaaa tgccaagtac tggtaaaact cctactctag gtttaaataa  32760
gtgggagtta acagataagc caaaaatgaa tgactttaat aaggataatg aaaacattga  32820
gaactttgct accgaacata aacagaaaat gactgaggta gaaaagaagt ctaagtctaa  32880
tgaggatagg ctagatgctt tgagggttgg tactattaat agacttgaat ggtataattc  32940
tgagtcttat acgggtcctg gtaatatcac atctattaca gatgctccaa ctaagagacg  33000
aggttttaaa tggtcaggta tgtcaacagg tccacaaatt cttgaaatta aaaccctgcc  33060
```

-continued

```
tatagaaccg aatagtgatt atgtactagc cttcctagag gatattgaag gtagttttac  33120
tagctatgag attaaactgg cttacactag tggaggccaa caatataaga gcattgtaaa  33180
gcaaggtagc acatcacaga gtaatgggta taaattaaaa actcataaat ttagtattcc  33240
ctctggagct actgatacta aaatacaatt tgtggtacag ggtgcaacct caagcacatc  33300
attaaaggta ctaaacctat tactagctag aggtaatgta gtacctgact ataacctagc  33360
ccctgaggat gtactgaaaa gactagacct attctttgag aaagatatta atttacaaaa  33420
ccaaataaat caaaaagctg ccaaagtgga tgtgatccaa agggtcgatg tacctgtgga  33480
tagggattgt aattccttta aagcaggaaa ctccttctgc tcctttgata tggggaatgg  33540
tgattttaaa aataccccctg agggaacact gccccagggg agtgctaggg tatttatctt  33600
aaggaatata ggtttaggtg atggtaagaa taggtttcaa caggagttta ttaatctata  33660
tccagatagt aacataaccc gatatattag aaattatatc tatgagagta actcatgggg  33720
taaatggtat aaggtttatg atgaagctaa taagccaaca ccacgagaat taggtgtagc  33780
tgcggttaat atgcccatgg ctgatacaga ccttaataac cataaggaac ctggatttta  33840
ttggggttat caaaatatgg tcaatgcccc tgtacccaat ggtgtagcaa ttatggaggt  33900
agttaagtat aataatgatt gtgtattaca aagatttacc tcagttagag cagatagtaa  33960
ccatactact tatattagaa cctgctattc aaataaatgg tctagctgga agaagattta  34020
tgatgagggt aataagccta ctccaatgga catagggggct tgggataaaa cagccaaaag  34080
actagagggt gtagatctaa acaccattac agagggggggt atttattcta cagttagaaa  34140
ttctattgaa aaaaatgccc caactctagc agatgggaga ttgattgttt tatcctggaa  34200
tacaggacac tgggcttctc aaatgttctt tgcagatggt ggaggagttt ttactagaac  34260
agctacaaac atggagggta ctggatggac gaattgggct gaaatatata gtaaacaaaa  34320
caaacctacc ccagctgata taggggcttc tcctagtaac cataatcata ataaggtata  34380
ttaccctata cctaaacagg ctattactga ttttaattcc ggtatagcta taactgaggg  34440
tcaacatcta gtatcttcta gtacagctat acctaattca cctcctttat atgctcaaga  34500
tggtagtagt atatatggta tacttcatgt atacgttagt gttggtgatt cttataatgg  34560
tgtgaataac tggatatggc aagactttca tgatactagg ggtaatcact actggaggta  34620
taaaattaat aatgctgact ggagtccttg gagagctgta tataattctg ttaataaacc  34680
aacccccccag gctatagggg ctgtagctac tgaaggtgat ggagtaataa atgggaaatt  34740
aactgtagac caaatagtca atgttagcac tgtgggagta ctagctagtc ttaggaatga  34800
taatatgaga gctttattat gtggagtagg aggaacagat gtatatctcc aaaataaaaa  34860
gtctaataaa tttttacagt taagagatga tggtgtatta gcttatagtg ggagtttaat  34920
ttatcatcaa aataataaac ccactccctc tgagatagga gcagcctctt caggccataa  34980
tcatgatagt gcttatttga agaaagaaga tacagctgct aatagtaata aacttaagaa  35040
ctgggactta gctgaaggga gtaataactt tgtgggtata ccatttatac cccatgatgg  35100
agtcatggag gtaggtagaa tggttgactt tcatgagtct ggatctgata aggattttaa  35160
tagtagatta gagtctatta atggagcctt aaagtgttgg caagacttct ctgctgaaaa  35220
tctatgggct aggaaatacc taagaataaa tgactggtat ggtggagctg aagatggaag  35280
attgtggttc aaacaagaga acaaaaagtt atatactgag aatattactg acttcgttgt  35340
aaatggtagg tctattgcta aaggagacta ttgggataat gacaatggta acgttagggt  35400
atgtcatctt gggggaggac taagattagt tcgtcaaata gttaagacgg gctatgctaa  35460
```

```
ctcaggtgga ggtgtaagtt atactataca tttctctaag gcttggaatt gggtattacc  35520
tatatctcta gtatcacata actataatga cgcttctaat aatacctcag gttattgtac  35580
tattgattat tggaataact catatttgaa tggtggatgt tatcaaatgg tagctggtaa  35640
gccaactcaa ataatactaa cctatttagc tactgggtaa gggagttgat aaaacatgag  35700
aatagtagga tttaattatt ctgtggaaac taataaggtt atagacctta tattctatga  35760
tgatgaaaaa gaaatgctga taaatcaggc agaagactca gaagatgtaa gatcatttat  35820
agataaagac catgaagaag ttactaaaat attagaccta attaatagac ctgaacctct  35880
atactataga gaggatagtg aaatattaaa taatatagaa gatattgtat gtctccatat  35940
accccataat tcacaagggc atttagcctt tgtggataac actgaggtta ttgatctaga  36000
caatcttcct gttatacaaa tgactgtaag tctatttgac cacataaaga gtggcccaac  36060
taaatttgat attagtaaaa agagatcaga tctatacagt atcaaagata aggacctatt  36120
tacttcatat gaggctatag atcctaatcc tctagatatt aataaattaa ttggttatca  36180
agcccaggct cttgctgata ctaaattaga gctaatgcaa actaaagcca taatgaaagt  36240
attaacacaa gaactagctg atataaaaat taaattgatg aataaataag gaggtagaga  36300
ttatgaattt ctgggaaatg gcttatagaa ttggagcaat aggtaaggac aaattacatc  36360
aggcagtaaa atgctcttct aatccagaag gagaaattac accagaggac tataaaagaa  36420
tatgtggtga agactttaat gaaagggtgt aatctatgga aaaagaacta ctaactcaag  36480
ttcttagcca aggtatcttt tgtagtctat ttgtatggct attatatgac actagaaaag  36540
aggctagaga aagagagaat aaattaaatc aagtgataga taagctagtt gataaattca  36600
acgtagttga ggatattaaa gaggatgtag atactataaa agatcaccta tttagtaaca  36660
aaggttaaat tataagccta gcaggccatt taaggcctgt taggttttat ataagaaaat  36720
atattaaggg ggtggttaaa gtgctgtagc gagcctctca ggcccaataa aaccctataa  36780
tatttaaagg agatgttaat tatgaaaatc aataaaagat taagtactac taatgttact  36840
ctagatgcaa ataatccaga gtatataatt atccacgaaa ctgataatac ctcttggggt  36900
gctggagctg aaacccactg taaggcccaa gcaaatggaa atataggtaa agccagtgtc  36960
cattattatg tcgatgatac aggggtatat caagctgtag aacacaaaca tgccacttgg  37020
aattgtggag atggtcataa tagatatggt atcaataata gaaatacaat atctatagaa  37080
atatgtgtta atcctgactc tgactacaat agagcagttg ataatgctgt agagctagtt  37140
agatatctaa agaatggcta ctattctaat tgtaaagtag taagacacta tgatgccagt  37200
agaaaaaatt gtcctagaag aatgatagcc aatggttact ggaatacatt cctagaaaga  37260
gtaaattcag gagagagctc aagctcacca ataatcaata accctaaagg attctatgag  37320
tctaatgaga caagaactaa tgctacttta gtaggggaag gttcaataga agttctagat  37380
gaggattgta agccagtccc tggtagattt attgatagcc tagataattt atttgttctt  37440
ggaatatatc cttccagaaa tttcatagaa gttgtatatc ctggaaagga taagaaatac  37500
catgcttaca ttgacataaa acattatagc agattaagtt ttgactacca catgaaatat  37560
caaaatgata atggaataac ttatgtgtgg tggaaccctg aagacattaa tgtcaaagat  37620
cataatgaag aattacagcc tggtcaaaag gctagcccaa tgtatagaac taagggctgg  37680
ttaagaataa cattttatag aaaggatggt actccatctg atggatacgt tcgttacgag  37740
ggtgagcaaa gccagaaatt ctatgaggat gttaaacaag gaatagttaa ggttaacact  37800
```

-continued

```
tctcttaatg taagagatga tgtgaatggt aatataatag gctcagtatc taataatgag  37860
agagttacta tattaggaag taagaatggt tggtatcata tagaatataa tactagccat  37920
ggtaagaagc aaggttatgt aagttcaaaa tatgtagaga taatttaggg ggtatttatc  37980
atggaagaaa atttagtaaa tttaatattc aattacattg atccacagct tttaataatc  38040
attgtatcat gttactgttt aggtctgttt atcaaggcta agccttatat accagattgg  38100
tctataccat taatactttt ggtattcagt atatcattgt caatcttata tatggcaatt  38160
cagttagaac taggttttac agctaagacc tttttgaatg gctttataca aggtttaata  38220
tgtgcagctg tagcttcctt tggtaatcaa gtatggaagc agttaatgga taagagaaaa  38280
tcagatcctc ctgtaaatca atagggggata gaggttgggc ctactttatt tagaaagtag  38340
gtccttaacc tttttaaatt cttcttcatt atcccattcc cattgctttc ctggttttac  38400
aacttctttg tttcttaaga ttcttcttgc ctttttacca ttcatattta attcttcaag  38460
tatcatcttt aatgtgaact taccttcctt agtttttggt tcagcttttg gttcatcctt  38520
tttctctggt tccttaacat ctgttagatc aagagtaatt ttagtttgtt cagccttttc  38580
ttcaggttca gctggttgtt gtacctcttc aactttttct tcttgtggtt gttggatttg  38640
ttggatagca gctattagat cagccttttt catagtccac cagtttttaa cttttaattc  38700
ctttgctaat tctttaattt caacagcttt catagtattt aaatctttca tatcatttac  38760
ctcttctttc ttatttgttt tatctacatt ttcattataa gagatttcct ctggtttgtc  38820
agggatttct tttaataatt ttggacctcc ccagttacat tcttctccat cagcattatc  38880
aaagaccttt cttccttctt ctgtgtaacc tattacctct ccatcagcaa atactaaacc  38940
ttttttaaca agtgatgaga tcacacctct agccttagtt ccttctatac ctgagttttc  39000
tattactgag aatacccata cacagtcaac atctagtccg tcatcaaatt cattctttct  39060
catagcattt aatatcttta tttccattgc agttaagttc atatttaaca tctcctcttt  39120
gtttttgttt acaagtttat tataagagtt attgccagag atgtcaaagg ttttctccac  39180
agatttataa aatttctttg agatcttagt tggtatcaca tatttaaagc cgttacattt  39240
aaagcaagta gtgttaccat ctgaggttct tgagtaatgg ccagtgcctc cacatctagg  39300
gcaagtttta agtaaacctt tcttagcaac ctttgacata gtgctagccc atatcttacc  39360
aaagccatat ttgattttag ctttatctga aaggtcaggg tacaccatat taattatatc  39420
accctttaat ggatcatcct tgatataact attataccaa tccaatttaa cttgggtatg  39480
tgatctccta cttattacct tagtaacctc atactccttt aaccatccat ctatggcctc  39540
attggataat ttatcagcct cttcaaaagt tatgctatta acaggtatac taaatgctcc  39600
tgttgctacc cagcttccat cttcttttg gcaaccaaag aagttttcag cttctacttg  39660
aataccataa tatatatcta tcatgtgatt tacctcctaa gttatttgtt aatataatta  39720
taccagcact ctcgagatat gtcaacgaaa aaagaggaga agttttacct tcttccccta  39780
acctttaagt tgattaatag atcatatata tctttaggca taccttgctc ccactcccat  39840
tgtttacctg gtttctcaat gttattcttt cttaatatac ttcttgcctt tcttggatct  39900
agttctatca attcacataa atcttttaaa gtgtatatat cacttctagt ttgtgctaca  39960
gctgagtttt caccttttct agcctgttgc actttgttgt aataaagact agttaatttt  40020
ttatgtaaag gactatgtga ccaataagtt aagtgagcta attcatggca tatagtttca  40080
agaacacagt ccttaatatt ccagccaaat tttttgattt tatcataagc tttttctcct  40140
tcctgtgcaa acctgaaagg gaaaagatta attgtaatcc cagtaaattt attacctgat  40200
```

ctatggcata gaccataata attggcatcc acatcagatt ctatataaag atcaacagca 40260
cttacaccaa atgcttttcc taagatcatt gtggcctcat tgtataactc ctttacttca 40320
tattcagcta attgattttc tatcatatct ctcattttgt ttacctccaa tagttaattt 40380
atgatttaat tataagagag aactctggat ctgtcaacga aaaacttcga agaaaaaaaa 40440
aggatggggt ttaccatcct agatcatctc ttcttcctat atcatatatt gcacagatgc 40500
aagcctcaag atgtttttca atctcagctt ttttatgatg tttacataca taatatttag 40560
ttactcccat ttgttgtaat agttctatct tcttatctaa gaattgtttt tggaagttct 40620
tttcaaaaac taccttctgt attttttcta tctcatttaa catttctaat ttagtcattt 40680
ttcattcctc ctaagaatta attaatattg attacaatat tattatacca gagggcccag 40740
actatgtcaa cgagattctg gagatttttc gaaaaaaata gatggccttt tggccaccca 40800
tattaattgg ctttttttcat ttttaggata acctcatcat aggcaaccat acagcaagaa 40860
aggtagtctc ctaattcact ttccctaact ttgttgctta gtccaaggga ttttacctgt 40920
ttatcaagtt cctttctaaa ttgtggatag attttattat ccatagcctt ttgagcaatt 40980
ccctttatta cattaagttt ttctgatctt gttagttcca tagttaacat ctccttagtt 41040
aattttgatt acaatattat tatactagat agtcccgacc ctgtcaacga ttaaatccag 41100
attttttcga aaaataaaaa ggaggttttt acacctcctt agttttatag atccttgaac 41160
atttcagggt agttacataa agtatcttcc acatattgtt ctgggtggta atcatattct 41220
atgatgtatt caacagcagc tattaagtca ttctcatcat taaattctac cccttgtatt 41280
tctagttcct cctttaattg ttctaaagtt tcttgaaatt ttttgttatt cataattaac 41340
aactcctttg aattaatttt gtttacaaga ttattatacc agactctgga gtccatgtca 41400
aagaaaatcc cgaatttctt ttttggcatg aaagttgcta ggtatcggat cgctttaaaa 41460
agaagcaact atttagttgc tcctatgggg gttaatgaaa accctgataa tttttttattc 41520
tttccccacc tagcacaagc ttccattgtg ggctcaatac ccaagatatt gcatatatcc 41580
aaatattctt ttaaccataa taacctcata ataattaatc ctcctttgag tatcttaact 41640
tcttagattt tttattctta tacatcattg agtcagcctg tactatggct tcttcaatag 41700
ttttaccttt accatagcca catgatagct cagggtatat attcaaggta ttgcatagat 41760
tataagctat atcactgata actacaaact catcaccacc ccacctaatc aatatatcct 41820
tctcaggatg taaatgggcc ttgataagat ttacagtgta ttgtatatac acatctcctt 41880
ctagatggcc taacttatca ttgaactctt tcagatcatt aagatcaata tatacaatct 41940
catactcctc aaggtcaatc ttatagtttc tattataggc tcctgtccaa tcaatagata 42000
actcctttac aagttcaatc aattcttccc ttgtaagttt ttcaagatct ttcatattca 42060
gttctctcct ttttgtttga ttacaatatt tatattacca tatactgtgg atattgtcaa 42120
cgaaaaagaa gaggttttta aacctccccc tattttaaca ttttcttaat atcctcaagt 42180
tcagatcctg accatttata tggtttgttt acaccttgct ttcttagctt ggccctggct 42240
ttacttggat ctaatcctaa tgactcacat aaagttttta agtcaactgt tccagtaggt 42300
gcattacctc cagaaggtgt agggtaagtt cccttagcct caactttatt cagatcaacc 42360
ttcttaagag gtttgtcctt tttctttctt ggcttcttag gctcattagg attaaattct 42420
ttcattaatt ctctctcctt cttcttttcc tcatttagga gtcttagcct ttcaaggcct 42480
ttttgttttt tcttttcctc cttgacttta atcttggtta gggccttaat agttttccca 42540

-continued

```
gcttcaatca aagctttagc tatttcagta tgattactta ttctaggttg ttcttttctc  42600
attatttatc acctcaattc tatattacca cattacttat cagtagtcaa cagtttttct  42660
gctctatccc ttttaagctg tattgatttt aatattttct catcaatagt attctcagtt  42720
attaagtgta ttatttgcca aggttccttt tgaccatttc ttttaattct ggcaatagct  42780
tgcacatagt catcatactt atagttccaa ctatagaata ttaaccttga ggccctgaag  42840
aggtttagac caacactacc tgaacttatt tgtagtatta atatgtcaat cttgccctcc  42900
tgaaaatcct tattgatctc agctctattc ttagtagatc ctgttaagca ttctactctg  42960
tgggtctttt taaaagtatc atgtataagt tttatttctt caagaaaatt acatattacc  43020
acaacaggtt ttttatatcc ttctagatag tcctgtaaca agcctaattt gcctttatca  43080
atgttaatac tatttcctac attgtttgta ataaatcctc ctgagatctg ctgtagcctt  43140
aaatattggg taatagtaag atcagctgtt aattgattga taaacatatt agctcttaag  43200
aataaatcct catatggctc attactctca taaggtatac cattagacct taataaggcc  43260
tttaattgct tcctaggaat gttttcctgt actatatcta gttgtgctat catttccttt  43320
ctaaggtcat tgtaggcctt tctagcttta ctatttagtt cacaggttaa atacagatca  43380
ggaagttgtt ctggtaaatc aatacaatct tctattctta ctatatagca attctggtgc  43440
ataaggttct ttaatatttc ctcattctta taccccacaa tttcatagtt catataacct  43500
cccttgatta taaagtcatc ctcaaactgt ttccagttaa ctcctagaat atttgagttc  43560
ataattttat attgcataaa taaatcttca taaccattag gagtaggagt ccctgtcatt  43620
atcaatctat atttacattt agtagcaatt ttatatagag ccttagatat ctgggcattt  43680
ctattcttta ccttatggga ttcgtcaaca acaataaact gtggctttaa gttcataagg  43740
tatttatcca tcaacctagc cttctcaaaa ttggcaataa taatctttaa tcctgagtat  43800
gattttatag ctctataagt ttccataacc ttggctttat taccttgtaa tttaaatatt  43860
ttatattcct taagtttagt aaatttatgg atctcagact cccagttaaa tacaatagac  43920
ttaggtgaga atattagtac agtatctaaa ccttcaagtt tctcaagggc cacaatagga  43980
actaaggtct tacccgtacc catgtccata aataaggcaa acttttcttt atttaaaaat  44040
agttgtaatg cttctttctg atgtttaaat aattttctct tcatactaaa aaagaagagg  44100
cattaaagcc tcctccttat acctccttag ccagttttac aagttcatct cttgaggcct  44160
tactatggaa tttaacccca ttatctttta ggtattgttt taaggattct ttattcatac  44220
tatcaaagtc taattcttct tcgtcgtaaa tgttatcatc atcctctaag tcctcatcgt  44280
cattatcatc tatgtcttct tcatcatatt cttctttact aagatcatgt atttctgagt  44340
tatcatcact agttaattcc atagcagcca taatagcata gttagctaag tctagtaaag  44400
tatcaaccac agattctttt tgagcagcat atgaagggaa gtcatcttga tctcctagta  44460
ataaactttt agctcttcct agcttatctt caagtcttat acataggaca gggtttccat  44520
attcaagata agtcttgtgg aaattatccc catatagatt attctttaat tcatacagat  44580
ctcctagttc tcctaggaat tgttggtgtc tttctaaatt tttcatgtaa tctcctcctt  44640
gtatattcag ctgaggtagc cataaaagct attcctcctg ctagatttat tttatttata  44700
atgtcttttt gtttttgagt taggttcttt tcttttccag gaagtttaac ttcaatacca  44760
ataaacttac ctttgtggca acctagtata tcaggtaagc cagctatttg aaatggtccc  44820
ccatgagttt taaaccaaaa accggggtat tcttttttaa gcatattcat tatggattta  44880
accacatctc tttcaagcat aatagtagcc tccaagggta aataaaggag gaccttaaag  44940
```

-continued

```
gccctcatat tttaataatt aaattttatt cttcatcatc ttcttctagc atttctatga  45000
tgtcatcctt agacattcct tttttaacct ttaagcctct gtccttagct tcagctttaa  45060
gttcttttaa agtcattgac tcatagtcat tttcttcttc atcttcctct tcttcatcag  45120
agtctccgaa taggtcatta tattgttcag ctatttcttc ttcgtcagct tcttcctcaa  45180
ttagatcaat tagatcttct tcagttttag ccttcttgat tttcttagct gggattttta  45240
aagccttagc taattctttt agctcatcct tgtctaattc ttcaagatca acttcagact  45300
catcgtcttc atcatcttct tcgtcatctg agtcatcatc ctcatcttcg tcatcatcag  45360
agtcagcttc gtcaaggttt ataaaatcag ttattcttga tttcttctta ccttcatata  45420
tttcatgtga tacttctacc ccacattgta aaccaactag agcttctgta tctaattcga  45480
actcctcatc agggatatca aatcctaaag caactaacac acctttttaag ttaaataaag  45540
cttgtggttg aagtgagcaa atgtggtata acttttgtcc tttcatcttt ccttctgcta  45600
ttacaaaagt aaatgataaa taattgcttc cactattttc agaaacctta acctctacat  45660
cttctacttc cacaatgtaa ttcccttctg ggatagtaac tgaagtttca acgtttgaaa  45720
gatcaatctt taatcctcct ttgtttttgt tacctctctt agtagtcttt ttagccatgt  45780
tattgtcctc cttaaatttt aaaatatcat tatgagataa atatttgtca agatattgta  45840
cctctttgtt tacaagttta tattatcaga tttttaattg gttgtcaaag gtatttttag  45900
aaaattttta ttttttcttt ttaccagatt tcttactggt ttttttacca gatttagctg  45960
gcttattatt ccattcacca gccagaatag tttcaatatc ctcccagata gttgttggtg  46020
attttaaatc atgtactaga taagctggac attcagatcc ttgaggtcta gtaaacttag  46080
taatataata ggggttaggt cccagtctta atctatactg gatttctttc ttaaccttca  46140
taccctcttt ttctgagtgt tcatataaat aagtatgacc tattactctt gatacagcac  46200
ataaatattt agatacagat ggcattaatc ctggtcctac ctcaggcatt aattggtctt  46260
ctccttctcc atcaccagat tctaatctat cttgtactat aaagcatggt agtatacctt  46320
cctcatttaa ttctttataa aggtttataa cctctttcat ataattagcc acatttccaa  46380
acattctttg gctcatctgg tctttgcctt cctcagcttt gaccttttca ttacctaatt  46440
cttgtaaagc agttaaatgg tctataacta ctgttttaaa tttatcagtg ttttctgata  46500
ggtaatcata agcctcgtat atgtcatcaa aactctttag actaaatact tgtatatctc  46560
ctcttttaac tctaagcttg tttctagctg atagagtacc tttgtccttt acatcaataa  46620
agaatattgg tttgggtagt gttcctgaga tggtagtttt acctgaacca gatcttccat  46680
aaagtgttaa tattgtgggc tcatctatat catatagatc cactaatctg tcctcaaaac  46740
tatttgattt tgatttttgc tttttgcca ttgtcacttt cctccctttg tctatagtca  46800
gccttaataa taaattcttt atcaagattt aaaagttcag cttgacataa agacttatat  46860
tcacagaaag agcaaccttt tccaaggttc ttttcctttc ttttgtggcc ctcatctcta  46920
ataagtttag ctatctcaat agtatcatcc attacactgt taagtatatt ctttgataat  46980
attattgggt gtcttacaaa gaagtcttcc catctagcag aattaatata ggactcataa  47040
tctttaggat ctaatcctaa ttcttttatt cccctttcta actctaaagg tgtggattta  47100
atcctctttt gagataatac cccttttttga gttaattcag gcctacctgg ttgctgagct  47160
aatattatat cccatatagt accacttact tttgggtatt catgtagaag agcccaggta  47220
tatatagcag attgtctatt gaagatcagg aaatttctat caggcatctt tttataggtt  47280
```

```
ttagtttcct tagcccatat ctttccatcc acatctaaga cactatcaat atagccttct  47340
aggtttacac ccttacatag ttttaattca aagtgatgtt cattttccac ataggttaca  47400
ttatcttctt tttcatcata atagtggaaa tagttatcac ataaagaata aaccattttt  47460
ggaatatctc caaattcaag gatctcttcc ttaaatgtat ttttgtaaaa ctctttggaa  47520
aatttatcaa cagatttttt ccaactcttc ccattatggt agtcttctat agcctggtgg  47580
atagcagagc ccctttgtaa ggcagctcca cttcttttag gtaccagacc ttcatagtac  47640
ttaacataat gggcataagg acaagacaag aatttgttaa ttctggaatt acttattttt  47700
aacatcctta tacctccttt tcattacaat atttatatta tcagataatt attcatctgt  47760
caacactttt cttatctggc ttttccaatc acctttaaaa tccagttcca cacatcctcc  47820
ccaagaataa ccaactgata tatccatgat tattgggact gttggagtaa atttaaatac  47880
tttctttaat accttattat tttcaactat tgattttact ttccaagcta attcttccac  47940
ataatcttta tctacttcaa ataatattga gtcatgtact gagcctaata catcaaactt  48000
agacttatct aatacatatt caggattaac atatttagca tagcctgtaa tctcacatag  48060
gcctaataaa gtgatatctg aaccaaaacc ttgaacaggt gagttaatac attgtctttc  48120
ggcttcagca gctttagatc tatcagatga atatatatct ggtaatcttc taattcttcc  48180
tattggagat cttacttcac cattggcttt aacaattttt ctttgtttat catgccatgt  48240
taatagttta gggtatttat taaagaagtt ccttctatat gttttggctt cctcatctgt  48300
taatttaagg ccatagttgt ctcttccata atccttgaac tttttccatt gcataccata  48360
taagaaacca aagtttacag ccttagcctt tttccttttc tccttcttaa ctgctggatc  48420
tttctcatca ttgatatctt ccccagatat aatattatat gtggagtcat gtatatctcc  48480
accagtctgg taaataaatt tcatattatc ctcatcggcc atcatagcag ctattctaag  48540
ttcggcctgg gatagatcgg cttcaatgaa tactcttcca ggagatggtc ctaataaact  48600
cctgattttc ttatctctag gaacttgctg tagattagga ttattacttg aggttcttcc  48660
tgttacagtt ccatgaagtt taaagtttgg atataatcta tgattgtgca ttctatttaa  48720
ccaaccatct ataaagtgag aaatttgtat atggactccc ctatgctgta atagtagttc  48780
tactgctgga tgtttatctc ttagtcttaa taatacactt tccccagtag caggtgctcc  48840
tgagtcagta acctcaatca caggaagacc aagggtatca tataaaaatt ctccaacctg  48900
tttaggtgag ctccagttaa tatccttacc attagtatac ttcttaagtc cagtctcaat  48960
cttatctagt tccgatctta agtatttttc aacctctttg aatttctcct gatttacata  49020
tatacctttg aactgaacat cctcataagc tttactagct gggatgtata agtggtggaa  49080
taatttatat aagctctcat ctcttttaag tctcttatta aatattttat atagagcaaa  49140
tgtatagtat atatcatatc ccagatatct aacataatcc tcaaagtctg atttagtctc  49200
cacatttcca gtctttaatt tcttatttat atcccagtct ttagcattac aatgtaataa  49260
agcattctcc ttaagaccat taggggtatt ctcatctaaa caatgtgagg ctagtaaagt  49320
atcaaaggtt atgattggct taataccata tttctccttt aagaaattat catcaaactt  49380
accattctgg gctatccttt ccttcatctc agaattaagt cttttaatca aggatttagc  49440
taatcttctt tgtgctatgg gcttacccct taatggacta tatttgactt ctaaaggcag  49500
tatatactgt acttgagtat taccaaaacc aaatagggta atgttattat taaacctatc  49560
taggcctcta gtttctatat catatgatac tctattataa ccttcctctc ttaaatattt  49620
gaaagcctgg tttaactctt tcatattggt aataagtttt atgttaagct ctggtaattc  49680
```

-continued

```
atgctcttta ccttttacca tggctttaaa attattaaag gcctgatcta caaattgtgc  49740
tttagttggg tcatatgcaa ctacacctgg tgaatagctg gcaataaact taaagccata  49800
tttctcatgc tttttaggta ctccacatat tgaggttata ccttcattac ttagcatctt  49860
taaggcttga gatcctaaga tcataacata ctcaggttta tatttttcaa tttccttaag  49920
taagtgttct tggcatttct taatctctga tactttgatt ttagtaccct taggagttct  49980
acacttaata gcattggtat aataaaagtc tagaccttcc attttatcaa gtaatgattt  50040
atcaggagta gctattctat tggcctcatc cctatcatta gctaaactat ttataaccat  50100
tattcttggc ttctttttct ttcctacaca agttccttct atacatgagg gagctgagtg  50160
agtatatagg ttacagttgt tacatctcat ttaaagtatt acctcctaaa tagaaaggac  50220
ccctaaaggc ccttatcttt actttatgat tgaattacat actggacaga ccttatgttt  50280
tttgaaaggt atggttacta cccataggcc tccagttaag aaaatcatga tccaaaacat  50340
agctccatat tttcttttta atgttactga gtttttacac ataggacaaa ttatattttt  50400
c                                                                   50401
```